(12) United States Patent
Cornmell et al.

(10) Patent No.: US 9,320,271 B2
(45) Date of Patent: Apr. 26, 2016

(54) MICROBIAL COMPOSITION

(71) Applicant: Rohm and Haas Company, Philadelphia, PA (US)

(72) Inventors: Robert J. Cornmell, Merseyside (GB); Megan A. Diehl, Line Lexington, PA (US); Stephen Golding, Merseyside (GB); John R. Harp, Knoxville, TN (US); Ian P. Stott, Merseyside (GB); Katherine M. Thompson, Merseyside (GB); Carol L. Truslow, Easton, PA (US)

(73) Assignee: Dow Global Technologies LLC, Midland, MI (US)

( * ) Notice: Subject to any disclaimer, the term of this patent is extended or adjusted under 35 U.S.C. 154(b) by 36 days.

(21) Appl. No.: 14/363,458

(22) PCT Filed: Dec. 5, 2012

(86) PCT No.: PCT/EP2012/074410
§ 371 (c)(1),
(2) Date: Jun. 6, 2014

(87) PCT Pub. No.: WO2013/083587
PCT Pub. Date: Jun. 13, 2013

(65) Prior Publication Data
US 2014/0356230 A1    Dec. 4, 2014

Related U.S. Application Data

(60) Provisional application No. 61/567,363, filed on Dec. 6, 2011, provisional application No. 61/567,380, filed on Dec. 6, 2011, provisional application No. 61/567,393, filed on Dec. 6, 2011, provisional application No. 61/567,351, filed on Dec. 6, 2011, provisional application No. 61/567,369, filed on Dec. 6, 2011, provisional application No. 61/664,775, filed on Jun. 27, 2012.

(51) Int. Cl.
| | | |
|---|---|---|
| *A62D 3/00* | (2007.01) | |
| *B01D 19/00* | (2006.01) | |
| *A61L 9/01* | (2006.01) | |
| *A01N 25/00* | (2006.01) | |
| *A01N 31/08* | (2006.01) | |
| *A01N 31/04* | (2006.01) | |
| *A61K 31/045* | (2006.01) | |
| *A61K 31/05* | (2006.01) | |
| *A61L 2/16* | (2006.01) | |

(52) U.S. Cl.
CPC ............... *A01N 31/08* (2013.01); *A01N 31/04* (2013.01); *A61K 31/045* (2013.01); *A61K 31/05* (2013.01); *A61L 2/16* (2013.01)

(58) Field of Classification Search
CPC .......... A61L 2/00; A01N 43/00; A01N 25/00; A01N 1/0215
USPC ............... 422/28; 252/186.1, 188.1; 424/405, 424/76.8
See application file for complete search history.

(56) References Cited

U.S. PATENT DOCUMENTS

| | | | |
|---|---|---|---|
| 2003/0180349 A1 | 9/2003 | Franklin | |
| 2005/0014827 A1 | 1/2005 | Schur | |
| 2008/0118591 A1 | 5/2008 | Natsch | |
| 2008/0194518 A1 | 8/2008 | Mookerjee et al. | |
| 2011/0081528 A1* | 4/2011 | Shannon | A47L 13/16 428/211.1 |

FOREIGN PATENT DOCUMENTS

| | | |
|---|---|---|
| WO | 2006/053458 A1 | 5/2006 |
| WO | 2008/126057 A2 | 10/2008 |
| WO | 2010/046238 A1 | 4/2010 |
| WO | 2010/070215 A1 | 6/2010 |

* cited by examiner

*Primary Examiner* — Monzer R Chorbaji
(74) *Attorney, Agent, or Firm* — Kenneth Crimaldi

(57) ABSTRACT

A synergistic microbicidal composition containing a phenolic compound selected from the class consisting of chlorinated phenols, monosubstituted phenols, fused bicyclic phenols, isopropyl methyl catechols, and monosubstituted catechols and an antimicrobial alcohol selected from the class of menthadiene alcohols and other antimicrobial alcohols.

9 Claims, No Drawings

MICROBIAL COMPOSITION

This invention relates to a synergistic combination of selected microbicides having greater activity than would be observed for the individual microbicides.

It particularly relates to an microbicidal composition for personal cleaning, oral care or hard surface cleaning or industrial and institutional cleaning applications.

In some cases, commercial microbicides cannot provide effective control of microorganisms, even at high use concentrations, due to weak activity against certain types of microorganisms, e.g., those resistant to some microbicides, or due to aggressive environmental, conditions.

For example, sanitising and disinfecting soap compositions comprising chlorine-based antimicrobial agent such as triclosan are known. Such compositions require a rather long contact time to provide efficacious antimicrobial action. In practice, users, in particular children, do not spend a long time on cleansing and as a result cleaning with such compositions does not provide adequate prevention from surface or topical infection or adequate protection against diseases. The user, in spite of cleaning his hands, is generally likely to end up with relatively inadequate bacterial removal from his skin. Therefore, he may cause contamination of further animate and/or inanimate surfaces and contribute to the spreading of pathogens and consequent diseases. Users in general and children in particular who wash contaminated hands before meals with slow-acting antimicrobial compositions for relatively short time are at risk of contracting diseases.

Similarly in the area of hard surface cleaning, e.g. cleaning of floors, table tops or utensils, the antimicrobial in the compositions are in contact with the substrate for less than a few minutes after which the surface is either wiped off or rinsed with water. These short time scales of cleaning action are ineffective in providing the desired benefit since most known antimicrobials commonly used in such products take many minutes to hours to provide the desired kill of microbes.

Therefore, there is a need of providing a composition that— upon application—provides relatively more efficacious antimicrobial action during a relatively short cleaning period, preferably about 30 seconds or less.

Combinations of different microbicides are sometimes used to provide overall control of microorganisms in a particular end use environment. For example, WO2010/046238 discloses combinations of thymol and terpineol. However, there is a need for additional combinations of microbicides having enhanced fast-acting activity against various strains of microorganisms to provide effective control of the microorganisms. Moreover, there is a need for combinations containing lower levels of individual microbicides for safety, environmental, aesthetic and economic benefit. The problem addressed by this invention is to provide such additional combinations microbicides.

STATEMENT OF THE INVENTION

The present invention is directed to a synergistic microbicidal composition, comprising: (a) at least one microbicide selected from the group consisting of 4-chloro-3,5-dimethylphenol, 2-hydroxydiphenylmethane, 4-hydroxydiphenylmethane, 2-benzyl phenol, 4-benzyl phenol; 5,6,7,8-tetrahydronaphthalen-1-ol, 5,6,7,8-tetrahydronaphthalen-2-ol; 2-cyclopentylphenol, 4-cyclopentylphenol, 3-isopropyl-6-methylbenzene-1,2-diol, 4-tert-butylbenzene-1,2-diol and (b) at least one microbicide selected from the group consisting of 2-(4-methylcyclohex-3-enyl)propan-1-ol, 4-(prop-1-en-2-yl)cyclohex-1-enyl)methanol, 2,4,6-trimethyl-3-cyclohexene-1-methanol, trans-4,6-dimethyl-3-cyclohexene-1-methanol, and 2,4-dimethylcyclohexylmethanol.

The present invention is further directed to a synergistic microbicidal composition, comprising: (a) 4-chloro-3,5-dimethylphenol; and (b) at least one microbicide selected from the group consisting of 2-(4-methylcyclohex-3-enyl)propan-1-ol, (4-(prop-1-en-2-yl)cyclohex-1-enyl)methanol, 2,4,6-trimethyl-3-cyclohexene-1-methanol, trans-4,6-dimethyl-3-cyclohexene-1-methanol, and 2,4-dimethylcyclohexylmethanol.

The present, invention is further directed to a synergistic microbicidal composition comprising: (a) at least one microbicide selected from the group consisting of 2-hydroxydiphenylmethane, hydroxydiphenylmethane, 4-hydroxydiphenylmethane, 2-benzyl phenol and 4-benzyl phenol; and (b) at least one microbicide selected from the group consisting of 2-(4-methylcyclohex-3-enyl)propan-1-ol, (4-(prop-1-en-2-yl)cyclohex-1-enyl)methanol, 2,4,6-trimethyl-3-cyclohexene-1-methanol, trans-4,6-dimethyl-3-cyclohexene-1-methanol, and 2,4-dimethylcyclohexylmethanol.

The present invention is further directed to a synergistic microbicidal composition comprising: (a) at least one microbicide selected from the group consisting of 5,6,7,8-tetrahydronaphthalen-1-ol and 5,6,7,8-tetrahydronaphthalen-2-ol; and (b) at least one microbicide selected from the group consisting of 2-(4-methylcyclohex-3-enyl)propan-1-ol, (4-(prop-1-en-2-yl)cyclohex-1-enyl)methanol, 2,4,6-trimethyl-3-cyclohexene-1-methanol, trans-4,6-dimethyl-3-cyclohexene-1-methanol, and 2,4-dimethylcyclohexylmethanol.

The present invention is further directed to a synergistic microbicidal composition comprising: (a) at least one microbicide selected from the group consisting of 2-cyclopentylphenol and 4-cyclopentylphenol; and (b) at least one microbicide selected from the group consisting of 2-(4-methylcyclohex-3-enyl)propan-1-ol, (4-(prop-1-en-2-yl)cyclohex-1-enyl)methanol, 2,4,6-trimethyl-3-cyclohexene-1-methanol, trans-4,6-dimethyl-3-cyclohexene-1-methanol, and 2,4-dimethylcyclohexylmethanol.

The present invention, is further directed to a synergistic microbicidal composition comprising: (a) at least one microbicide selected from the group consisting of 3-isopropyl-6-methylbenzene-1,2-diol and 4-tert-butylbenzene-1,2-diol; and (b) at least one microbicide selected from the group consisting of 2-(4-methylcyclohex-3-enyl)propan-1-ol, (4-(prop-1-en-2-yl)cyclohex-1-enyl)methanol, 2,4,6-trimethyl-3-cyclohexene-1-methanol, trans-4,6-dimethyl-3-cyclohexene-1-methanol, and 2,4-dimethylcyclohexylmethanol.

DETAILED DESCRIPTION OF THE INVENTION

As used herein, the following terms have the designated definitions, unless the contest clearly indicates otherwise. The term "microbicide" refers to a compound capable of killing, inhibiting the growth of or controlling the growth of microorganisms at a locus; microbicides include bactericides, fungicides and algaecides. The term "microorganism" includes, for example, fungi (such as yeast and mold), bacteria and algae. The following abbreviations are used throughout the specification: mL=milliliter, ATCC=American Type Culture Collection, and MBC=minimum biocidal concentration. Unless otherwise specified, temperatures are in degrees centigrade (° C.), and references to percentages are by weight (wt %).

The compositions of the present invention unexpectedly have been found to provide enhanced microbicidal efficacy at a combined active ingredient level lower than that of the individual microbicides. Additional microbicides beyond those listed in the claims may be present in the composition. The present invention provides for a synergistic antimicrobial composition comprising a phenolic compound and an antimicrobial alcohol preferably a terpene alcohol. The phenolic compound is preferably selected from the class consisting of chlorinated phenols, monosubstituted phenols, fused bicyclic phenols, isopropyl methyl catechols, and monosubstituted catechols. The antimicrobial alcohol is preferably selected from the class of menthadiene alcohols and other antimicrobial alcohols.

The compounds claimed as combinations in the present invention and the class they belong to are given below:
Menthadiene Alcohol
2-(4-methylcyclohex-3-enyl)propan-1-ol
4-(prop-1-en-2-yl)cyclohex-1-enyl)methanol
Other Antimicrobial Alcohol
2,4,6-trimethyl-3-cyclohexene-1-methanol
trans-4,6-dimethyl-3-cyclohexene-1-methanol
2,4-dimethylcyclohexylmethanol.
Chlorinated Phenol
4-chloro-3,5-dimethylphenol;
Monosubstituted Phenol
2-hydroxydiphenylmethane
4-hydroxydiphenylmethane
2-cyclopentylphenol
4-cyclopentylphenol
2-benzyl phenol
4-benzyl phenol
Fused Bicyclic Phenol
5,6,7,8-tetrahydronaphthalen-1-ol
5,6,7,8-tetrahydronaphthalen-2-ol;
Isopropyl Methyl Catechol
3-isopropyl-6-methylbenzene-1,2-diol
Monosubstituted Catechol
4-tert-butylbenzene-1,2-diol
Monosubstituted phenols generally have the following structure

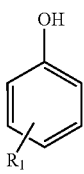

wherein
the substituent $R_1$ is selected from the group consisting of
linear $C_3$ to $C_5$ alkyl
isopropyl
branched $C_4$ alkyl,
linear $C_3$ to $C_5$ alkenyl,
linear $C_4$ or $C_5$ alkadienyl,
branched $C_4$ alkenyl,
cyclopentyl,
cyclopentenyl,
cyclohexyl,
cyelohexenyl,
phenyl, and
benzyl.

The fused bicyclic phenols have the following structure

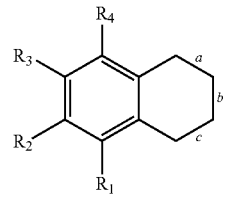

wherein, one of the substituents selected from $R_1$ and $R_3$ is a hydroxyl group;
and wherein the substituents $R_3$, $R_4$ and the substituent selected from $R_1$ and $R_2$ that is not a hydroxyl group, are independently selected from hydrogen, linear or branched $C_1$ to $C_6$ alkyl, linear or branched $C_1$ to $C_6$ alkenyl, cyclopentyl, cyclopentenyl, cyclohexyl, cyelohexenyl, phenyl, and benzyl;
and wherein the bonds a, b, and c are of the order one or two, such that at most one of a, b, and c is of the order two.

Thus, exactly one of $R_1$ and $R_2$ is a hydroxy group, the other being selected from the group as specified above.
Isopropyl-methylcatechols have the following structure

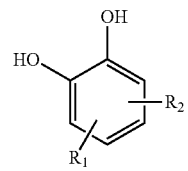

wherein R1 is a methyl group, and R2 is an isopropyl group.
Monosubstituted catechols have the following structure

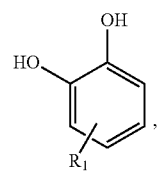

wherein the substituent $R_1$ is selected from the group consisting of linear $C_2$ to $C_5$ alkyl, branched $C_3$ to $C_5$ alkyl, linear $C_3$ to $C_5$ alkenyl, linear $C_4$ to $C_5$ alkadienyl, branched $C_4$ alkenyl, cyclopentyl, cyclopentenyl, cyclohexyl, cyclohexenyl, phenyl, and benzyl.

Monosubstituted catechols are also called monosubstituted benzene-1,2-diols or monosubstituted 2-hydroxyphenols.

The one or more antimicrobial alcohols have the following structure:

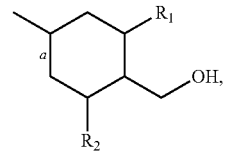

whereby
bond (a) is a single bond or a double bond, and
$R_1$ and $R_2$ are selected from methyl and hydrogen, with the proviso that at least one of $R_1$ and $R_2$ is methyl.

Among the monosubstituted phenols the preferred compounds are 2-cyclopentylphenol and 4-cyclopentyl phenol. Among the fused bicyclic phenols, the preferred compound is 5,6,7,8-tetrahydronaphthalen-1-ol. Among the isopropyl methyl catechol the preferred compound is 3-isopropyl-6-methylbenzene-1,2,-diol. The above phenolic compounds are especially preferred since they are evaluated by the present inventors to be more safe for use in consumer products.

Among the antimicrobials from the menthadiene alcohol class, 4-(prop-1-en-2-yl)cyclohex-1-enyl)methanol (perillyl alcohol) is preferred since it are evaluated by the present inventors to be safe for use in consumer products.

(4S) 4-(prop-1-en-2-yl)cyclohex-1-enyl)methanol form of 4-(prop-1-en-2-yl)cyclohex-1-enyl)methanol is especially preferred.

A preferred aspect of the present invention, is directed to a synergistic microbicidal composition comprising: (a) at least one microbicide selected from the class consisting of 5,6,7,8-tetrahydronaphthalen-1-ol and 5,6,7,8-tetrahydronaphthalen-2-ol; and (b) 4-(prop-1-en-2-yl)cyclohex-1-enyl)methanol.

Another preferred, aspect is directed to a synergistic microbicidal composition comprising: (a) at least one microbicide selected from the group consisting of 2-cyclopentylphenol and 4-cyclopentylphenol; and (b) 4-(prop-1-en-2-yl)cyclohex-1-enyl)methanol.

In a preferred embodiment of the invention, the synergistic antimicrobial composition comprises 4-chloro-3,5-dimethylphenol and 2-(4-methylcyclohex-3-enyl)propan-1-ol. Preferably, a weight ratio of 4-chloro-3,5-dimethylphenol to 2-(4-methylcyclohex-3-enyl)propan-1-ol is from 1/0.05 to 1/2.5, preferably from 1/0.19 to 1/2.5, preferably from 1/0.25 to 1/2.5.

In a preferred embodiment of the invention, the synergistic antimicrobial composition comprises 4-chloro-3,5-dimethylphenol and (4S)-(4-(prop-1-en-2-yl)cyclohex-1-enyl)methanol (also known as (S)-(−)-perillyl alcohol). Preferably, a weight ratio of 4-chloro-3,5-dimethylphenol to (4S)-4-(prop-1-en-2-yl)cyclohex-1-enyl)methanol is from 1/0.03 to 1/50, preferably from 1/0.03 to 1/0.08 or 1/0.13 to 1/50, preferably from 1/0.1.3 to 1/50, preferably from 1/0.13 to 1/0.67 or 1/1.5 to 1/50.

In a preferred embodiment of the invention, the synergistic antimicrobial composition comprises 4-chloro-3,5-dimethylphenol and 2,4,6-trimethyl-3-cyclohexene-1-methanol (also known as iso-cyclogeraniol). Preferably, a weight ratio of 4-chloro-3,5-dimethylphenol to 2,4,6-methyl-3-cyclohexene-1-methanol is from 1/0.13 to 1/6, preferably 1/0.13 to 1/0.17 or 1/0.33 to 1/6, preferably from 1/0.13 to 1/0.17 or 1/3 to 1/6.

In a preferred embodiment of the invention, the synergistic antimicrobial composition comprises 2-hydroxydiphenylmethane and 2-(4-methylcyclohex-3-enyl)propan-1-ol. Preferably, a weight ratio of 2-hydroxydiphenylmethane to 2-(4-methylcyclohex-3-enyl)propan-1-ol is from 1/0.04 to 1/0.08.

In a preferred embodiment of the invention, the synergistic antimicrobial composition comprises 4-hydroxydiphenylmethane and 2-(4-methylcyclohex-3-enyl)propan-1-ol. Preferably, a weight ratio of 4-hydroxydiphenylmethane to 2-(4-methylcyclohex-3-enyl)propan-1-ol is from 1/0.08 to 1/0.5, preferably from 1/0.1 to 1/0.5, preferably from 1/0.25 to 1/0.5.

In a preferred embodiment of the invention, the synergistic antimicrobial composition comprises 2-hydroxydiphenylmethane and (4S)-(4-(prop-1-en-2-yl)cyclohex-1-enyl) methanol. Preferably, a weight ratio of 2-hydroxydiphenylmethane to (4S)-(4-(prop-1-en-2-yl)cyclohex-1-enyl) methanol is from 1/0.06 to 1/0.5, preferably from 1/0.25 to 1/0.5, preferably from 1/0.38 to 1/0.5.

In a preferred embodiment of the invention, the synergistic antimicrobial composition comprises 2-hydroxydiphenylmethane and 2,4,6-trimethyl-3-cyclohexene-1-methanol. Preferably, a weight ratio of 2-hydroxydiphenylmethane to 2,4,6-trimethyl-3-cyclohexene-1-methanol is from 1/0.05 to 1/1.5, preferably from 1/1 to 1/1.5.

In a preferred embodiment of the invention, the synergistic antimicrobial composition comprises 4-hydroxydiphenylmethane and 2,4,6-trimethyl-3-cyclohexene-1-methanol. Preferably a weight ratio of 4-hydroxydiphenylmethane to 2,4,6-trimethyl-3-cyclohexene-1-methanol is from 1/0.10 to 1/10, preferably from 1/1 to 1/10, preferably from 1/7.5 to 1/30.

In a preferred embodiment of the invention, the synergistic antimicrobial composition comprises 5,6,7,8-tetrahydronaphthalen-1-ol and 2-(4-methylcyclohex-3-enyl)propan-1-ol. Preferably, a weight ratio of 5,6,7,8-tetrahydronaphthalen-1-ol to 2-(4-methylcyclohex-3-enyl)propan-1-ol is from 1/0.19 to 1/0.5, preferably from 1/0.25 to 1/0.5.

In a preferred embodiment of the invention, the synergistic antimicrobial composition comprises 5,6,7,8-tetrahydronaphthalen-2-ol and 2-(4-methylcyclohex-3-enyl)propan-1-ol. Preferably, a weight ratio of 5,6,7-tetrahydronaphthalen-2-ol to 2-(4-methylcyclohex-3-enyl)propan-1-ol is from 1/0.04 to 1/0.33, preferably from 1/0.1 to 1/0.33.

In a preferred embodiment of the invention, the synergistic antimicrobial composition comprises 5,6,7,8-tetrahydronaphthalen-1-ol and (4S)-(4-(prop-1-en-2-yl)cyclohex-1-enyl)methanol. Preferably, a weight ratio of 5,6,7,8-tetrahydronaphthalen-1-ol to (4S)-4-(prop-1-en-2-yl)cyclohex-1-enyl)methanol is from 1/0.15 to 1/10, preferably from 1/0.1.9 to 1/10.

In a preferred embodiment of the invention, the synergistic antimicrobial composition comprises 5,6,7,8-tetrahydronaphthalen-2-ol and (4S)-(4-(prop-1-en-2-yl)cyclohex-1-ethyl)methanol. Preferably, a weight ratio of 5,6,7,8-tetrahydronaphthalen-2-ol to (4S)-(4-(prop-1-en-2-yl)cyclohex-1-enyl)methanol is from 1/0.15 to 1/5, preferably from 1/0.19 to 1/5.

In a preferred embodiment of the invention, the synergistic antimicrobial composition, comprises 5,6,7,8-tetrahydronaphthalen-1-ol and 2,4,6-trimethyl-3-cyclohexene-1-methanol. Preferably, a weight ratio of 5,6,7,8-tetrahydronaphthalen-1-ol to 2,4,6-trimethyl-3-cyclohexene-1-methanol from 1/0.15 to 1/5, preferably from 1/0.25 to 1/5.

In a preferred embodiment of the invention, the synergistic antimicrobial composition comprises 5,6,7,8-tetrahydronaphthalen-2-ol and 2,4,6-trimethyl-3-cyclohexene-1-methanol. Preferably, a weight ratio of 5,6,7,8-tetrahydronaphthalen-2-ol to 2,4,6-trimethyl-3-cyclohexene-1-methanol is from 1/0.04 to 1/10, preferably from 1/0.04 to 1/0.15 or 1/0.19 to 1/10, preferably from 1/0.19 to 1/10.

In a preferred embodiment of the invention, the synergistic antimicrobial composition comprises 2-cyclopentylphenol and 2-(4-methylcyclohex-3-enyl)propan-1-ol. Preferably, a weight ratio of 2-cyclopentylphenol to 2-(4-methylcyclohex-3-enyl)propan-1-ol is from 1/0.25 to 1/2.5.

In a preferred embodiment of the invention, the synergistic antimicrobial composition comprises 4-cyclopentylphenol and 2-(4-methylcyclohex-3-enyl)propan-1-ol. Preferably, a weight ratio of 4-cyclopentylphenol to 2-(4-methylcyclohex-3-enyl)propan-1-ol is from 1/0.33 to 1/3.33.

In a preferred embodiment of the invention, the synergistic antimicrobial composition comprises 2-cyclopentylphenol and (4S)-(4-(prop-1-en-2-yl)cyclohex-1-enyl)methanol.

Preferably, a weight ratio of 2-cyclopentylphenol to (4S)-(4-prop-1-en-2-yl)cyclohex-1-enyl)methanol is from 1/0.3.8 to 1/50. More preferably, a weight ratio of 2-cyclopentylphenol to (4S)-(4-(prop-1-en-2-yl)cyclohex-1-enyl)methanol is either from 1/0.38 to 1/2 or from 1/3.75 to 1/50.

In a preferred embodiment of the invention, the synergistic antimicrobial composition comprises 4-cyclopentylphenol and (4-(prop-1-en-2-yl)cyclohex-1-enyl)methanol. Preferably, a weight ratio of 4-cyclopentylphenol to (4-(prop-1-en-2-yl)cyclohex-1-enyl)methanol is from 1/0.06 to 1/2.5. More preferably, a weight ratio of 4-cyclopentylphenol to (4-(prop-1-en-2-yl)cyclohex-1-enyl)methanol is from 1/0.5 to 1/2.5.

In a preferred embodiment of the invention, the synergistic antimicrobial composition comprises 2-cyclopentylphenol and 2,4,6-trimethyl-3-cyclohexene-1-methanol. Preferably, a weight ratio of 2-cyclopentylphenol to 2,4,6-trimethyl-3-cyclohexene-1-methanol is from 1/0.06 to 1/3. More preferably, a weight ratio of 2-cyclopentylphenol to 2,4,6-trimethyl-3-cyclohexene-1-methanol is either from 1/0.06 to 1/0.17 or from 1/0.33 to 1/3.

In a preferred embodiment of the invention, the synergistic antimicrobial composition comprises 4-cyclopentylphenol and 2,4,6-trimethyl-3-cyclohexene-1-methanol. Preferably, a weight ratio of 4-cyclopentylphenol to 2,4,6-trimethyl-3-cyclohexene-1-methanol is from 1/0.5 to 1/1.25. More preferably, a weight ratio of 4-cyclopentylphenol to 2,4,6-trimethyl-3-cyclohexene-1-methanol is from 1/0.75 to 1/2.5.

In a preferred embodiment of the invention, the synergistic antimicrobial composition comprises 3-isopropyl-6-methylbenzene-1,2-diol and 2-(4-methylcyclohex-3-enyl)propan-1-ol. Preferably, a weight ratio of 3-isopropyl-6-methylbenzene-1,2-diol to 2-(4-methylcyclohex-3-enyl)propan-1-ol is from 1/0.03 to 1/0.13. More preferably, a weight ratio of 3-isopropyl-6-methylbenzene-1,2-diol to 2-(4-methylcyclohex-3-enyl)propan-1-ol is either 1/0.03 or 1/0.13.

In a preferred embodiment of the invention, the synergistic antimicrobial composition comprises 4-tert-butylbenzene-1,2-diol and 2-(4-methylcyclohex-3-enyl)propan-1-ol. Preferably, a weight ratio of 4-tert-butylbenzene-1,2-diol to 2-(4-methylcyclohex-3-enyl)propan-1-ol is 1/0.13.

In a preferred embodiment of the invention, the synergistic antimicrobial composition comprises 3-isopropyl-6-methylbenzene-1,2-diol and (4S)-(4-(prop-1-en-2-yl)cyclohex-1-enyl)methanol. Preferably, a weight ratio of 3-isopropyl-6-methylbenzene-1,2-diol to (4S)-(4-(prop-1-en-2-yl)cyclohex-1-enyl)methanol is from 1/0.13 to 1/150. More preferably, a weight ratio of 3-isopropyl-6-methylbenzene-1,2-diol to (4S)-(4-(prop-1-en-2-yl)cyclohex-1-enyl)methanol is from 1/1 to 1/150.

In a preferred embodiment of the invention, the synergistic antimicrobial composition comprises 4-tert-butylbenzene-1,2-diol and (4S)-(4-(prop-1-en-2-yl)cyclohex-1-enyl)methanol. Preferably, a weight ratio of 4-tert-butylbenzene-1,2-diol to (4-(prop-1-en-2-yl)cyclohex-1-enyl)methanol is from 1/0.03 to 1/0.17. More preferably, a weight ratio of 4-tert-butylbenzene-1,2-diol to (4S)-(4-(prop-1-en-2-yl)cyclohex-1-enyl)methanol is either 1/0.03 or 1/0.13.

In a preferred embodiment of the invention, the synergistic antimicrobial composition comprises 3-isopropyl-6-methylbenzene-1,2-diol and 2,4,6-trimethyl-3-cyclohexene-1-methanol. Preferably, a weight ratio of 3-isopropyl-6-methylbenzene-1,2-diol to 2,4,6-trimethyl-3-cyclohexene-1-methanol is from 1/0.08 to 1/75. More preferably, a weight ratio of 3-isopropyl-6-methylbenzene-1,2-diol to 2,4,6-trimethyl-3-cyclohexene-1-methanol is either from 1/0.08 to 1/0.13 or from 1/1 to 1/75.

In a preferred embodiment of the invention, the synergistic antimicrobial composition comprises 4-tert-butylbenzene-1,2-diol and 2,4,6-trimethyl-3-cyclohexene-1-methanol. Preferably, a weight ratio of 4-tert-butylbenzene-1,2-diol to 2,4,6-trimethyl-3-cyclohexene-1-methanol is from 1/0.03 to 1/3.75. More preferably, a weight ratio of 4-tert-butylbenzene-1,2-diol to 2,4,6-trimethyl-3-cyclohexene-1-methanol is either from 1/0.04 to 1/0.06 or from 1/0.75 to 1/3.75.

Combinations according to the invention are capable of very fast antimicrobial action. For instance, we found that complete microbial inactivation could be effected with compositions according to the present invention, in most cases, after a contact time of only 15 seconds.

The microbicides in the composition of this invention may be used "as is" or may first be formulated with a solvent or a solid carrier. Suitable solvents include, for example, water; glycols, such as ethylene glycol, propylene glycol, diethylene glycol, dipropylene glycol polyethylene glycol, and polypropylene glycol; glycol ethers; alcohols, such as methanol ethanol, propanol, phenethyl alcohol and phenoxypropanol; ketones, such as acetone and methyl ethyl ketone; esters, such as ethyl acetate, butyl acetate, triacetyl citrate, and glycerol triacetate; carbonates, such as propylene carbonate and dimethyl carbonate; inorganic particulate material, starch, air and mixtures thereof. In certain preferred embodiments, suitable solvents include for example water, glycols, glycol ethers, esters and mixtures thereof. Suitable solid carriers include, for example, cyclodextrin, silicas, clays, talc, calcite, dolomite, aluminosilicate, diatomaceous earth, waxes, cellulosic materials, alkali and alkaline earth (e.g., sodium, magnesium, potassium) metal salts (e.g., chloride, nitrate, bromide, sulfate) and charcoal.

Particularly preferred carriers are water or oil/solvent and even more preferred is a carrier that is a mixture of water and oil. Examples of oils include mineral oils, oils of biological origin, (e.g. vegetable oils), and petroleum-derived oils and waxes. The oils of biological origin are preferably triglyceride-based. Preferably, the carrier oil is not a perfume oil. Thus, the carrier oil preferably does not substantially contribute to the odour of the composition, more preferably it does not contribute to that odour. Examples of solvents include alcohols, ethers and acetone. The starch may be natural starch obtained from food grains or may be a modified starch.

Air can for instance be used as a carrier when the components according to the invention and/or the terpineol are atomised or otherwise dispersed as a fine mist.

Particularly preferred carriers are water or oil/solvent and even more preferred is a carrier that is a mixture of water and oil. Thus, in many of the envisaged applications like personal care/washing, oral care and hard surface cleaning, the antimicrobial composition may be formulated with either an aqueous base or an oil/solvent base. Compositions with an aqueous base (water being the carrier), can also for instance be products in gel format. Compositions with an oil/solvent base can for instance be products in anhydrous stick form or propellant-containing products.

Thus, the antimicrobial composition, can for instance, preferably be an antimicrobial, anhydrous stick personal care composition on an oil/solvent base wherein the composition has a water content of less than 0.01% by weight, and wherein the composition preferably is free of water. Alternatively, the antimicrobial composition can for instance, preferably be an antimicrobial propellant-drivable personal care composition, also comprising a propellant. Air can also be used as propellant, for instance in the form of compressed or liquefied air. However, the most preferred product format has an emulsion base (water and/or oil being the carrier) or is capable of forming an emulsion upon dilution, e.g. soap products in liquid, solid, lotion or semisolid form for band wash, face wash, body wash, or shaving applications; toothpaste/dentifrices for oral care applications or products for hard surface cleaning in bars or liquids form. If the product comprises an emulsion base, it preferably also comprises one or more surfactants as described below.

"Substantially free" means, e.g., having less than 5 wt % based on the weight of active ingredients (i.e., the weight of claimed components a) and b) plus the additional ingredients listed in this paragraph), preferably less than 3 wt %, preferably less than 1 wt %, preferably less than 0.5 wt %, preferably less than 0.2 wt %.

When a microbicide component is formulated in a solvent the formulation may optionally contain surfactants. When such formulations contain surfactants, they can be in the form of emulsive concentrates, emulsions, microemulsive concentrates, or microemulsions. Emulsive concentrates form emulsions upon the addition of a sufficient amount of water. Microemulsive concentrates form microemulsions upon the addition of a sufficient amount of water. Such emulsive and microemulsive concentrates are generally well known in the art. U.S. Pat. No. 5,444,078 may be consulted for further general and specific details on the preparation of various microemulsions and microemulsive concentrates. A preferred product format has an emulsion base (water and/or oil being the carrier) or is capable of forming an emulsion upon dilution, e.g. soap products in liquid, solid, lotion or semisolid form for hand wash, face wash, body wash, or shaving applications; toothpaste/dentifrices for oral care applications or products for hard surface cleaning in bars or liquids form. If the product comprises an emulsion base, it preferably also comprises one or more surfactants as described below.

It is particularly preferred that the microbicidal composition comprises from 1 to 80% by weight of one or more surfactants in addition to the synergistic combination of microbiocides claimed in the present invention.

In general, the surfactants may be chosen from the surfactants described in well-known textbooks like "Surface Active Agents" Vol. 1, by Schwartz & Perry, Interscience 1949, Vol. 2 by Schwartz, Perry & Berch, Interscience 1958, and/or the current edition of "McCutcheon's Emulsifiers and Detergents" published by Manufacturing Confectioners Company or in "Tenside-Taschenbuch", H. Stache, 2nd Edn., Carl Hauser Verlag, 1981; "Handbook of Industrial Surfactants" (4th Edn.) by Michael Ash and Irene Ash; Synapse Information Resources, 2008. Any type of surfactant, i.e. anionic, cationic, nonionic, zwitterionic or amphoteric can be used. Preferably, the one or more surfactants are anionic, nonionic, or a combination of anionic and nonionic surfactants. More preferably, the one or more surfactants are anionic.

A particularly preferred surfactant is soap. Soap is a suitable surfactant for personal washing applications of the antimicrobial composition of the invention. The soap is preferably $C_8$-$C_{24}$ soap, more preferably a $C_{10}$-$C_{20}$ soap and most preferably $C_{12}$-$C_{16}$ soap. The soap may or may not have one or more carbon-carbon double bonds or triple bonds. The cation of the soap can for instance be an alkali metal, alkaline earth metal or ammonium. Preferably, the cation of the soap is selected from sodium, potassium or ammonium. More preferably the cation of the soap is sodium or potassium.

The soap may be obtained by saponifying a fat and/or a fatty acid. The fats or oils may be fats or oils generally used in soap manufacture, such as tallow, tallow stearines, palm oil, palm stearines, soya bean oil, fish oil, castor oil, rice bran oil, sunflower oil, coconut oil, babassu oil, palm kernel oil, and others. In the above process the fatty adds are derived from oils/fats selected from coconut, rice bran, groundnut, tallow, palm, palm kernel, cotton seed, soyabean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources. Other similar mixtures, such as those from palm oil and those derived from various animal tallow and lard are also included.

A typical fatty acid blend consists of 5 to 30%-wt coconut fatty acids and 70 to 95%-wt fatty acids ex hardened rice bran oil. Fatty acids derived from other suitable oils/fats such as groundnut, soybean, tallow, palm, palm kernel, etc. may also be used in other desired proportions. The soap, when present in solid forms of the present invention, is preferably present in an amount of 30 to 80%, more preferably from 50 to 80%, and even more preferably 55 to 75% by weight of the composition. The soap, when present in liquid forms of the composition is preferably present in 0.5 to 20%, more preferably from 1 to 10% by weight of the composition.

Other preferred surfactants fatty acid glycinates and fatty amphocarboxylates. These surfactants are particularly preferred in skin and hair cleaning compositions, because of their mild detergency and highly foaming nature. The fatty acid glycinates are salts of fatty acid amides of glycine, including for example sodium cocoyl glycinate. The fatty amphocarboxylates are amphoteric surfactants including for example sodium lauroamphoacetate (i.e. sodium 2-[1-(2-hydroxyethyl)-2-undecyl-4,5-dihydroimidazol-1-ium-1-yl]acetate). Yet another example of suitable surfactants are derivatives of isethionates, including acylisethionates.

The antimicrobial composition of the invention is also useful in hard surface cleaning applications. In such applications, preferred surfactants are nonionic surfactants, such as $C_8$-$C_{22}$, preferably $C_8$-$C_{16}$ fatty alcohol, ethoxylates, comprising between 1 and 8 ethylene oxide groups when the product is in the liquid form. When the product for hard surface cleaning applications is in the solid form, surfactants are preferably selected from primary alkyl sulphates, secondary alkyl sulphonates, alkyl benzene sulphonates, ethoxylated alkyl sulphates, or alcohol ethoxylate nonionic surfactants. The composition may further comprise an anionic surfactant, such as alkyl ether sulphate preferably those having between 1 and 3 ethylene oxide groups, either from natural or synthetic source and/or sulphonic acid. Especially preferred are sodium lauryl ether sulphates. Alkyl polyglucoside may also be present in the composition, preferably those having a carbon chain length between C6 and C16. Other classes of useful surfactants include cationic surfactants, such as long chain quaternary ammonium compounds and amphoteric surfactants such as betaines and alkyl dimethyl amine oxides. Suitable surfactant concentrations in liquid forms of hard surface cleaning application are generally from about from 0.5 to 10%, preferably from 1 to 5% by weight of the composition. In solid compositions, surfactant is preferably present in 5 to 40%, preferably from 10 to 30% by weight of the composition.

The antimicrobial composition of the invention is useful in oral care compositions e.g. in a dentifrice/toothpaste or an oral rinse product. In such applications, preferred surfactants are anionic, nonionic or amphoteric in nature, preferably anionic or amphoteric. The anionic surfactant is preferably an alkali metal alkyl sulphate, more preferably a sodium lauryl sulphate (SLS). Mixtures of anionic surfactants may also be employed. The amphoteric surfactant is preferably a betaine, more preferably an alkylamidopropyl betaine (wherein the alkyl group is a linear $C_{10}$-$C_{18}$ chain), and most preferably is cocoamidopropyl betaine (CAPB). Mixtures of amphoteric surfactants may also be employed. Suitable surfactant concentrations in oral care application are generally from about 2% to about 15%, preferably from about 2.2% to about 10%, more preferably from about 2.5 to about 5% by weight of the total composition.

Thus, it is highly preferred that the antimicrobial compositions include soap, alkyl sulphate or linear alkyl benzene sulphonate as the surfactants. More preferably, the one or more surfactants are selected from the group consisting of soaps, alkyl sulphates and linear alkyl benzene sulphonates. A microbicide component also can be formulated in the form of a dispersion. The solvent component of the dispersion can be an organic solvent or water, preferably water. Such dispersions can contain adjuvants, for example, co-solvents, thickeners, anti-freeze agents, dispersants, fillers, pigments, surfactants, biodispersants, polycations, stabilizers, scale inhibitors and anti-corrosion additives.

When both microbicides are each first formulated with a solvent, the solvent used for the first microbicide may be the same as or different from the solvent used to formulate the other commercial microbicide, although water is preferred for most industrial biocide applications. It is preferred that the two solvents are miscible.

The composition may further comprise various additional ingredients known to a person skilled in the art. Such additional ingredients include but are not limited to: perfumes, pigments, preservative, emollients, sunscreens, emulsifiers, gelling agents, thickening agents, humectants (e.g. glycerine, sorbitol), sequestrants (e.g. EDTA) or polymers (e.g. cellulose derivatives for structuring such as methyl cellulose)

The antimicrobial composition may be in form of a solid, a liquid, a gel or a paste. A person skilled in the art can prepare compositions in various formats by choosing one or more carrier materials and/or surfactant. The antimicrobial compositions of the present invention are useful for cleansing and care, in particular for skin cleansing and skin care. It is envisaged that the antimicrobial composition can be used as a leave-on product or a wash-off product, preferably a wash-off product. The antimicrobial composition of the present invention can also be used for cleansing and care of hard surfaces such as glass, metal, plastic and the like.

Those skilled in the art will recognize that the microbicide components of the present invention may be added to a locus sequentially, simultaneously, or may be combined before being added to the locus. It is preferred that the first microbicide and the second microbicide component be added to a locus simultaneously or sequentially. When the microbicides are added simultaneously or sequentially, each individual component may contain adjuvants, such as, for example, solvent, thickeners, anti-freeze agents, colorants, sequestrants (such as ethylenediamine-tetraacetic acid, ethylenediaminedisuccinic acid, iminodisuccinic acid and salts thereof), dispersants, surfactants, biodispersants, polycations, stabilizers, scale inhibitors and anti-corrosion additives.

The microbicide compositions of the present invention can be used to inhibit the growth of or kill microorganisms by introducing a microbicidally effective amount of the compositions onto, into or at a locus subject to attack.

Suitable loci include, for example: industrial process water including electrocoat deposition systems, cooling towers and air washers; gas scrubbers; wastewater treatment; ornamental fountains; reverse osmosis filtration; ultrafiltration; ballast water; evaporative condensers and heat exchangers; pulp and paper processing fluids and additives; mineral slurries; starch; plastics; emulsions; dispersions; paints; latices; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household and institutional products used in restaurants, healthcare facilities, schools, food, processing facilities and farms including, cleaners, sanitizers and disinfectants, wipes, soaps, detergents, floor polishes and laundry rinse water; cosmetics; toiletries; shampoos; metalworking fluids; conveyor lubricants; hydraulic fluids; leather and leather processing products; textiles; textile and textile processing products; wood and wood processing products, such as plywood, chipboard, wallboard, flakeboard, laminated beams, oriented strandboard, hardboard, and particleboard; oil and gas processing fluids such as injection fluids, fracture fluids, drilling muds and produced water; fuel transportation and storage systems; agriculture adjuvant preservation; surfactant preservation; medical devices; diagnostic reagent preservation; food preservation, such as plastic or paper food wrap; food, beverage, and industrial process pasteurizers; toilet bowls; recreational water; pools; and spas.

In preferred embodiments, the composition is particularly suited for application to the skin. For example, a surface like the hands, face, body, or the oral cavity can suitably be contacted with the composition of the invention. In other preferred embodiments, the surface is any hard surface. Typically, such hard surfaces are surfaces that commonly require cleaning and often also require sanitization or disinfection. Such surfaces can be found in many household or industrial environments, and can include for example kitchen and bathroom surfaces, table tops, floors, walls, windows, utensils, cutlery, and crockery. Such, surfaces can be made from many different materials, for instance plastics, wood, metal, ceramics, glass, concrete, marble, and painted surfaces. In preferred embodiments, the compositions can be used for such disinfection, reduction in microbial count or improved hygiene at loci other than the surfaces as described hereinbefore.

In preferred embodiments, the invention relates to compositions according to the invention for use as or incorporation in home care products and personal care products. More preferably, this embodiment of the invention relates to a composition according to the invention which is a home care product or a personal care product.

A. "home care product" is a product used for the treatment, cleaning, caring or conditioning of the home or any of its contents. The foregoing includes, but is not limited to, compositions, products, or combinations thereof relating to or having use or application in the treatment, cleaning, cleansing, caring or conditioning of surfaces, furniture and atmosphere of the home and household contents, such as clothes, fabrics and/or cloth fibers and the manufacture of all of the foregoing products. A "personal care product" is a product for the treatment, cleaning, caring or conditioning of the person. The foregoing includes, but is not limited to, chemicals, compositions, products, or combinations thereof relating to or having use or application in the treatment, cleaning, cleansing or conditioning of the person (including in particular the skin, hair and oral cavity), and the manufacture of all the foregoing. Home care products and personal care products are for example products marketed under mass market brands, non-limiting examples being soap bars, deodorants, shampoos, and home-surface sanitizers/disinfectants.

According to a another aspect of the invention, there is provided a method of disinfecting a surface comprising the steps of a. applying a composition according to the invention on to the surface; and b. removing the composition from the surface.

The method according to the present invention also includes the step of removing the composition from the surface. Here, removing the composition also encompasses partially removing the composition, because traces of the composition may remain on the surface. In many typical situations, such as washing of the skin, or hard-surface cleaning, it is acceptable or sometimes even desirable if part of the composition—in particular certain active ingredients—remains on the surface. Therefore, step b preferably involves removing at least 5%, more preferably at least 10%, even more preferably at least 25%, still more preferably at least 50% and yet more preferably at least 75% of the composition, by weight. Preferably, the step of removing the composition comprises rinsing the surface with a suitable solvent or wiping the surface with a suitable wipe, more preferably, this step consists of rinsing the surface with a suitable solvent or wiping the surface with a suitable wipe. Alternatively, the removal step can also include evaporation of part of the composition, for example when the composition comprises volatile components, e.g. solvents.

A suitable medium for rinsing the surface is water but it could also be for example a mixture of water and alcohol. It is then rinsed preferably with sufficient amounts of water after a pre-determined period of time to remove any visible or sensory residue of the composition. Alternatively, an alcohol wipe or a water/alcohol impregnated wipe may be used to wipe the surface to be visibly free of the anti-microbial composition. The step of removing the composition (e.g. by rinsing or wiping the surface) is preferably started less than 5 minutes, more preferably less than 2 minutes, even more preferably less than 1 minute, still more preferably less than 30 seconds and yet more preferably less than 20 seconds after commencement of the step of applying the composition on the surface, because of the surprisingly fast antimicrobial action of the compositions according to the present invention. Even though partial microbial kill may be almost instantaneous upon application of the composition according to the invention, it is preferred that the step of removing the composition from the surface is started put at least 5 seconds, preferably at least 10 seconds, more preferably at least 15 seconds after commencement of the step of applying the composition on the surface, in order to effect optimal antimicrobial action. Combinations of these times into time intervals are preferred too. Therefore, it is particularly preferred that the step of removing the composition from the surface (i.e. step b) is started between 2 minutes and 5 seconds, more preferably between 1 minute and 10 seconds, even more preferably between 30 and 10 seconds and still more preferably between 20 and 15 seconds after commencement of the step of applying the composition on the surface (i.e. step a).

Disinfection Time

These times between applying the composition and rinsing or wiping are preferably related to the disinfection time, in order to ensure optimal cleansing and sanitising of the surface. Therefore, the invention preferably relates to a method, wherein the disinfection time T of said method is less than 300 seconds, preferably less than 60 seconds, and more preferably less than 15 seconds; wherein T is defined as the time that elapses from the moment of adding the composition to a microbial culture until the number of microbes per unit volume of the culture is reduced by a factor of 100 000; and wherein the initial number of microbes preferably exceeds about 100 000 000 microbes per milliliter and wherein the composition is preferably a liquid composition.

The disinfecting action of the method (as may be expressed in terms of the disinfection time T) is preferably determined according to the protocol of Example 1 as described hereinafter. This test relates to a standardised test environment in which the microbial culture is kept in suspension. A similarly suitable test is the standard suspension method described in European Standard EN1276, with the proviso that the disinfection time is adapted to suit the above criteria as will be clear to a person skilled in the art. Alternatively, one of the test methods as described in WO 2010/046238 may for instance be applied to establish the disinfecting action.

Such test methods may preferably also be used by the skilled person to determine the optimal concentrations of the one or more components in an antimicrobial composition according to the present invention.

Alternatively, since the method is directed towards surface disinfection, the disinfection time may also be determined by test methods involving a surface. Therefore, the invention preferably relates to a method according to the present invention, wherein the surface disinfection time T2 of said method is less than 60 seconds, preferably less than 15 seconds, wherein T2 is defined as the time starting from the moment of applying the composition to the surface to be disinfected after which the number of microbes per unit area is reduced by a factor of 10000 (i.e. a 4 log reduction), wherein the initial number of microbes preferably exceeds $10^3$ more preferably $10^5$, and even more preferably $10^7$ microbes per square centimeter. Such tests may for instance be performed as described in WO 2010/046238, or as described in European Standards EN 13697:2001 and EN 1500:1997.

Another preferred embodiment of the invention relates to compositions according to the invention for use as or incorporation in industrial and/or institutional products. More preferably, this embodiment of the invention relates to a composition according to the invention which is an industrial and/or an institutional product. Industrial and institutional products are for example products being marketed under professional brands, non-limiting examples being for industrial, institutional, janitorial, and medical cleaning, cleaning-in-place, food services, veterinary, and agricultural products. Industrial and/or institutional products also include products for cleaning of the person (such as hand sanitizers) for medical offices, hospitals and/or other institutions.

In another preferred embodiment, the invention also relates to a method or use according to the invention involving home care products or personal care products. For example, the method according to the invention—which comprises application of a composition according to the invention in step a—can be a method wherein that composition is a composition for use as or incorporation in home care products and personal care products as described hereinabove. Similarly, in another preferred embodiment, the invention also relates to a method or use according to the invention involving industrial and/or institutional products. For example, the method according to the invention—which comprises application of a composition according to the invention in step a—can be a method wherein that composition is a composition for use as or incorporation in industrial and/or institutional products as described hereinabove.

Products and/or methods for use in the home care or personal care field are generally distinct from products and/or methods for use in the industrial and/or institutional field. Thus, for example, a product that is marketed as a home or personal care product will generally not be marketed as a product for industrial and/or institutional use and vice versa.

Therefore, certain preferred embodiments of the present invention, when carried forth into practice, will relate to the one field, but not the other.

The specific amount of the composition of this invention necessary to inhibit or control the growth of microorganisms in a locus depends upon the particular locus to be protected. Typically, the amount of the composition of the present invention to control the growth of microorganisms in a locus is sufficient if it provides a total of from 0.02 to 4% of the microbicide ingredients of the composition in the locus. It is preferred that the microbicide ingredients of the composition be present in the locus in an amount of at least 0.05%, preferably at least 0.1%, preferably at least 0.2%, preferably at least 0.3%, preferably at least 0.4%. It is preferred that the microbicide ingredients of the composition be present in the locus at a total amount of no more than 4%, preferably no more than 2%, preferably no more than 1%.

If the surface is a surface of a human or animal body, the method preferably is a non-therapeutic method of disinfecting a surface.

EXAMPLES

Materials and Methods

The synergy of the combinations of the present invention was demonstrated by testing a wide range of concentrations and ratios of the compounds against the noted organism. One skilled in the art will recognize that the sensitivity of other microorganisms to the particular combinations will vary and, as a result, the concentrations, the ratios, for each, or both, of the compounds may vary from those detailed in these examples. The concentrations and ratios may also vary under different test conditions or with different test methods.

One measure of synergy is the industrially accepted method described by Kull, F. C.; Eisman, P. C.; Sylwestrowicz, H. D, and Mayer, R. L., in *Applied Microbiology* 9:538-541 (1961), using the ratio determined by the formula:

$$Q_a/Q_A = Q_b/Q_B = \text{Synergy Index ("SI")}$$

wherein;

$Q_A$=concentration of compound A (first component) in percent, acting alone, which produced an end point (MBC of Compound A).

$Q_a$=concentration of compound A in percent, in the mixture, which produced an end point.

$Q_B$=concentration of compound B (second component) in percent, acting alone, which produced an end point (MBC of Compound B).

$Q_b$=concentration of compound B in percent, in the mixture, which produced an end point.

When the sum of $Q_a/Q_A$ and $Q_b/Q_B$ is greater than one, antagonism is indicated. When the sum is equal to one, additivity is indicated, and when less than one, synergy is demonstrated. The lower the SI, the greater is the synergy shown by that particular mixture. The minimum biocidal concentration (MBC) of a microbicide is the lowest concentration tested under a specific set of conditions that provides complete kill of the tested microorganisms.

Synergy tests were conducted using standard microliter plate assays with phosphate buffer containing 35% dipropylene glycol (DPG). In this method, a wide range of combinations of chemicals was tested by conducting high resolution MBC assays of Component (A) in the presence of various concentrations of Component (B). High resolution MBCs were determined by adding varying amounts of microbicide to one column of a microliter plate and doing subsequent ten-fold dilutions using an automated liquid handling, system to obtain a series of closely spaced endpoints. The MBC plate was inoculated one column at a time with the test microorganism. An aliquot of the inoculated well was transferred at 15 seconds to a plate containing a neutralizing agent (D/E Neutralizing Broth), mixed and held for 5 minutes before being transferred to a growth plate containing trypticase soy broth (TSB). The TSB plate was incubated at 37° C. and read for the presence/absence of growth at 24 hours. The lowest level tested that provided complete kill (as evidenced by no growth in the microtitre plate) of the test organisms in 15 seconds is the minimum biocidal concentration (MBC).

The synergy of the combinations of the present invention was determined against a bacterium, *Escherichia coli* (*E. coli*—ATCC #10536), at a concentration of approximately $1 \times 10^8$ it bacteria per mL. This microorganism is representative of natural contaminants in many consumer and industrial applications. The plates were visually evaluated for microbial growth (turbidity) to determine the MBC after 24 hours incubation time at 37° C.

The test results for demonstration of synergy of the combinations of the present invention are shown below in Tables 1 through 26. Each table shows the specific combinations of the two components; results against the microorganism tested; the end-point activity in weight % measured by the MBC for the first component alone ($Q_A$), for the second component alone ($Q_B$), for the first component in the mixture ($Q_a$) and for the second component in the mixture ($Q_b$); the calculated SI value; and the range of synergistic ratios for each combination tested (first component to second component or A/B) against the particular microorganism.

Data in the tables below include the range of ratios that were found to be synergistic. (Data which were collected for combinations where concentrations were equal to or greater than $Q_A$ or $Q_B$ are not reported.) These data demonstrate that certain combinations of components A and B show enhanced control over the microorganisms than would be expected if the combinations were additive rather than synergistic.

TABLE 1

First Component (A) = 4-chloro-3,5-dimethylphenol
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.6 | 0 | 1.00 | |
| | 0.5 | 0.025 | 0.92 | 1 to 0.05 |
| | 0.5 | 0.05 | 1.00 | 1 to 0.1 |
| | 0.3 | 0.075 | 0.75 | 1 to 0.25 |
| | 0.4 | 0.075 | 0.92 | 1 to 0.19 |
| | 0.2 | 0.1 | 0.67 | 1 to 0.5 |
| | 0.3 | 0.1 | 0.83 | 1 to 0.33 |
| | 0.08 | 0.2 | 0.80 | 1 to 2.5 |
| | 0.1 | 0.2 | 0.83 | 1 to 2 |
| | 0 | 0.3 | 1.00 | |

The ratios of 4-chloro-3,5-dimethylphenol to 2-(4-methylcyclohex-3-enyl)propan-1-ol tested ranged from 1/0.025 to 1/250. The synergistic ratios of 4-chloro-3,5-dimethylphenol 2-(4-methylcyclohex-3-enyl)propan-1-ol range from 1/0.05 to 1/2.5.

TABLE 2

First Component (A) = 4-chloro-3,5-dimethylphenol
Second Component (B) = (4S)-(4-(prop-1-en-2-yl)cyclohex-1-enyl)methanol

| Microorganism | $Q_a$ | $Q_b$ | SI | Ratio A to B |
|---|---|---|---|---|
| E. coli 10536 | 1.0 | 0 | 1.00 | |
| | 0.6 | 0.025 | 0.65 | 1 to 0.04 |
| | 0.8 | 0.025 | 0.85 | 1 to 0.03 |
| | 0.3 | 0.05 | 0.40 | 1 to 0.17 |
| | 0.4 | 0.05 | 0.50 | 1 to 0.13 |
| | 0.6 | 0.05 | 0.70 | 1 to 0.08 |
| | 0.8 | 0.05 | 0.90 | 1 to 0.06 |
| | 0.3 | 0.075 | 0.45 | 1 to 0.25 |
| | 0.4 | 0.075 | 0.55 | 1 to 0.19 |
| | 0.5 | 0.075 | 0.65 | 1 to 0.15 |
| | 0.6 | 0.075 | 0.75 | 1 to 0.13 |
| | 0.8 | 0.075 | 0.95 | 1 to 0.09 |
| | 0.3 | 0.1 | 0.50 | 1 to 0.33 |
| | 0.4 | 0.1 | 0.60 | 1 to 0.25 |
| | 0.5 | 0.1 | 0.70 | 1 to 0.2 |
| | 0.6 | 0.1 | 0.80 | 1 to 0.17 |
| | 0.1 | 0.2 | 0.50 | 1 to 2 |
| | 0.2 | 0.2 | 0.60 | 1 to 1 |
| | 0.3 | 0.2 | 0.70 | 1 to 0.67 |
| | 0.4 | 0.2 | 0.80 | 1 to 0.5 |
| | 0.006 | 0.3 | 0.61 | 1 to 50 |
| | 0.008 | 0.3 | 0.61 | 1 to 37.5 |
| | 0.01 | 0.3 | 0.61 | 1 to 30 |
| | 0.02 | 0.3 | 0.62 | 1 to 15 |
| | 0.03 | 0.3 | 0.63 | 1 to 10 |
| | 0.04 | 0.3 | 0.64 | 1 to 7.5 |
| | 0.05 | 0.3 | 0.65 | 1 to 6 |
| | 0.06 | 0.3 | 0.66 | 1 to 5 |
| | 0.08 | 0.3 | 0.68 | 1 to 3.75 |
| | 0.1 | 0.3 | 0.70 | 1 to 3 |
| | 0.2 | 0.3 | 0.80 | 1 to 1.5 |
| | 0.3 | 0.3 | 0.90 | 1 to 1 |
| | 0 | 0.5 | 1.00 | |

The ratios of 4-chloro-3,5-dimethylphenol to (4S)-(4-(prop-1-en-2-yl)cyclohex-1-enyl)methanol tested ranged from 1/0.025 to 1/250. The synergistic ratios of 4-chloro-3,5-dimethylphenol to (4S)-(4-(prop-1-en-2-yl)cyclohex-1-enyl)methanol range from 1/0.03 to 1/50.

TABLE 3

First Component (A) = 4-chloro-3,5-dimethylphenol
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 0.5 | 0 | 1.00 | |
| | 0.3 | 0.05 | 0.68 | 1 to 0.17 |
| | 0.4 | 0.05 | 0.88 | 1 to 0.13 |
| | 0.3 | 0.075 | 0.73 | 1 to 0.25 |
| | 0.4 | 0.075 | 0.93 | 1 to 0.19 |
| | 0.2 | 0.1 | 0.57 | 1 to 0.5 |
| | 0.3 | 0.1 | 0.77 | 1 to 0.33 |
| | 0.4 | 0.1 | 0.97 | 1 to 0.25 |
| | 0.05 | 0.3 | 0.60 | 1 to 6 |
| | 0.06 | 0.3 | 0.62 | 1 to 5 |
| | 0.08 | 0.3 | 0.66 | 1 to 3.75 |
| | 0.1 | 0.3 | 0.70 | 1 to 3 |
| | 0.2 | 0.3 | 0.90 | 1 to 1.5 |
| | 0 | 0.6 | 1.00 | |

The ratios of 4-chloro-3,5-dimethylphenol to 2,4,6-trimethyl-3-cyclohexene-1-methanol tested ranged from 1/0.025 to 1/400. The synergistic ratios of 4-chloro-3,5-dimethylphenol to 2,4-trimethyl-3-cyclohexene-1-methanol range from 1/0.13 to 1/6.

TABLE 4

First Component (A) = 2-hydroxydiphenylmethane
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.8 | 0 | 1.00 | |
| | 0.6 | 0.025 | 0.85 | 1 to 0.04 |
| | 0.6 | 0.05 | 0.95 | 1 to 0.08 |
| | 0.6 | 0.075 | 1.05 | 1 to 0.13 |
| | 0 | 0.25 | 1.00 | |

The ratios of 2-hydroxydiphenylmethane to 2-(4-methylcyclohex-3-enyl)propan-1-ol tested ranged from 1/0.025 to 1/350. The synergistic ratios of 2-hydroxydiphenylmethane to 2-(4-methylcyclohex-3-enyl)propan-1-ol range from 1/0.04 to 1/0.08.

TABLE 5

First Component (A) = 4-hydroxydiphenylmethane
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.8 | 0 | 1.00 | |
| | 0.5 | 0.05 | 0.83 | 1 to 0.1 |
| | 0.6 | 0.05 | 0.95 | 1 to 0.08 |
| | 0.5 | 0.05 | 0.83 | 1 to 0.1 |
| | 0.5 | 0.075 | 0.93 | 1 to 0.15 |
| | 0.2 | 0.1 | 0.65 | 1 to 0.5 |
| | 0.3 | 0.1 | 0.78 | 1 to 0.33 |
| | 0.4 | 0.1 | 0.90 | 1 to 0.25 |
| | 0 | 0.25 | 1.00 | |

The ratios of 4-hydroxydiphenylmethane to 2-(4-methylcyclohex-3-enyl)propan-1-ol tested ranged from 1/0.025 to 1/350. The synergistic ratios of 4-hydroxydiphenylmethane to 2-(4-methylcyclohex-3-enyl)propan-1-ol range from 1/0.08 to 1/0.5.

TABLE 6

First Component (A) = 2-hydroxydiphenylmethane
Second Component (B) = (4S)-(4-(prop-1-en-2-yl)cyclohex-1-enyl)methanol

| Microorganism | $Q_a$ | $Q_b$ | SI | Ratio A to B |
|---|---|---|---|---|
| E. coli 10536 | 0.5 | 0 | 1.00 | |
| | 0.4 | 0.025 | 0.88 | 1 to 0.06 |
| | 0.4 | 0.05 | 0.97 | 1 to 0.13 |
| | 0.2 | 0.075 | 0.65 | 1 to 0.38 |
| | 0.3 | 0.075 | 0.85 | 1 to 0.25 |
| | 0.2 | 0.1 | 0.73 | 1 to 0.5 |
| | 0.3 | 0.1 | 0.93 | 1 to 0.33 |
| | 0 | 0.3 | 1.00 | |

The ratios of 2-hydroxydiphenylmethane to (4S)-(4-(prop-1-en-2-yl)cyclohex-1-enyl)methanol tested ranged from 1/0.025 to 1/400. The synergistic ratios of 2-hydroxydiphenylmethane to (4S)-(4-(prop-1-en-2-yl)cyclohex-1-enyl)methanol range from 1/0.06 to 1/0.5.

TABLE 7

First Component (A) = 2-hydroxydiphenylmethane
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 0.6 | 0 | 1.00 | |
| | 0.5 | 0.025 | 0.86 | 1 to 0.05 |
| | 0.4 | 0.1 | 0.77 | 1 to 0.25 |
| | 0.5 | 0.1 | 0.93 | 1 to 0.2 |

TABLE 7-continued

First Component (A) = 2-hydroxydiphenylmethane
Second Component (B) = 2,4,6-trimethyl-3-cyclohexene-1-methanol

| Microorganism | $Q_a$ | $Q_b$ | SI | Ratio A to B |
|---|---|---|---|---|
| | 0.2 | 0.3 | 0.63 | 1 to 1.5 |
| | 0.3 | 0.3 | 0.80 | 1 to 1 |
| | 0.4 | 0.3 | 0.97 | 1 to 0.75 |
| | 0.3 | 0.6 | 1.10 | 1 to 2 |
| | 0.2 | 0.8 | 1.13 | 1 to 4 |
| | 0 | 1 | 1.00 | |

The ratios of 2-hydroxydiphenylmethane to 2,4,6-trimethyl-3-cyclohexene-1-methanol tested ranged from 1/0.025 to 1/400. The synergistic ratios of 2-hydroxydiphenylmethane to 2,4,6-trimethyl-3-cyclohexene-1-methanol range from 1/0.05 to 1/1.5.

TABLE 8

First Component (A) = 4-hydroxydiphenylmethane
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 0.6 | 0 | 1.00 | |
| | 0.5 | 0.05 | 0.90 | 1 to 0.1 |
| | 0.5 | 0.1 | 0.96 | 1 to 0.2 |
| | 0.2 | 0.3 | 0.71 | 1 to 1.5 |
| | 0.3 | 0.3 | 0.88 | 1 to 1 |
| | 0.06 | 0.6 | 0.85 | 1 to 10 |
| | 0.08 | 0.6 | 0.88 | 1 to 7.5 |
| | 0.1 | 0.6 | 0.92 | 1 to 6 |
| | 0 | 0.8 | 1.00 | |

The ratios of 4-hydroxydiphenylmethane to 2,4,6-trimethyl-3-cyclohexene-1-methanol tested ranged from 1/0.025 to 1/490. The synergistic ratios of 4-hydroxydiphenylmethane to 2,4,6-trimethyl-3-cyclohexene-1-methanol range from 1/0.1 to 1/10.

TABLE 9

First Component (A) = 5,6,7,8-tetrahydronaphthalen-1-ol
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.6 | 0 | 1.00 | |
| | 0.5 | 0.05 | 1.03 | 1 to 0.1 |
| | 0.3 | 0.075 | 0.80 | 1 to 0.25 |
| | 0.4 | 0.075 | 0.97 | 1 to 0.19 |
| | 0.2 | 0.1 | 0.73 | 1 to 0.5 |
| | 0.3 | 0.1 | 0.90 | 1 to 0.33 |
| | 0 | 0.25 | 1.00 | |

The ratios of 5,6,7,8-tetrahydronaphthalen-1-ol to 2-(4-methylcyclohex-3-enyl)propan-1-ol tested ranged from 1/0.025 to 1/350. The synergistic ratios of 5,6,7,8-tetrahydronaphthalen-1-ol to 2-(4-methylcyclohex-3-enyl)propan-1-ol range from 1/0.19 to 1/0.5.

TABLE 10

First Component (A) = 5,6,7,8-tetrahydronaphthalen-2-ol
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.8 | 0 | 1.00 | |
| | 0.6 | 0.025 | 0.85 | 1 to 0.04 |
| | 0.4 | 0.05 | 0.70 | 1 to 0.13 |

TABLE 10-continued

First Component (A) = 5,6,7,8-tetrahydronaphthalen-2-ol
Second Component (B) = 2-(4-methylcyclohex-3-enyl)propan-1-ol

| Microorganism | $Q_a$ | $Q_b$ | SI | Ratio A to B |
|---|---|---|---|---|
| | 0.5 | 0.05 | 0.83 | 1 to 0.1 |
| | 0.6 | 0.05 | 0.95 | 1 to 0.08 |
| | 0.3 | 0.05 | 0.58 | 1 to 0.17 |
| | 0.4 | 0.05 | 0.70 | 1 to 0.13 |
| | 0.5 | 0.075 | 0.93 | 1 to 0.15 |
| | 0.3 | 0.1 | 0.78 | 1 to 0.33 |
| | 0.4 | 0.1 | 0.90 | 1 to 0.25 |
| | 0 | 0.25 | 1.00 | |

The ratios of 5,6,7,8-tetrahydronaphthalen-2-ol to 2-(4-methylcyclohex-3-enyl)propan-1-ol tested ranged from 1/0.025 to 1/3.50. The synergistic ratios of 5,6,7,8-tetrahydronaphthalen-2-ol to 2-(4-methylcyclohex-3-enyl)propan-1-ol range from 1/0.04 to 1/0.33.

TABLE 11

First Component (A) = 5,6,7,8-tetrahydronaphthalen-1-ol
Second Component (B) = (4S)-(4-(prop-1-en-2-yl)cyclohex-1-enyl)methanol

| Microorganism | $Q_a$ | $Q_b$ | SI | Ratio A to B |
|---|---|---|---|---|
| E. coli 10536 | 0.6 | 0 | 1.00 | |
| | 0.3 | 0.075 | 0.63 | 1 to 0.25 |
| | 0.4 | 0.075 | 0.79 | 1 to 0.19 |
| | 0.5 | 0.075 | 0.96 | 1 to 0.15 |
| | 0.3 | 0.1 | 0.67 | 1 to 0.33 |
| | 0.4 | 0.1 | 0.83 | 1 to 0.25 |
| | 0.03 | 0.3 | 0.55 | 1 to 10 |
| | 0.04 | 0.3 | 0.57 | 1 to 7.5 |
| | 0.05 | 0.3 | 0.58 | 1 to 6 |
| | 0.06 | 0.3 | 0.60 | 1 to 5 |
| | 0.07 | 0.3 | 0.62 | 1 to 4.3 |
| | 0.08 | 0.3 | 0.63 | 1 to 3.75 |
| | 0.1 | 0.3 | 0.67 | 1 to 3 |
| | 0.2 | 0.3 | 0.83 | 1 to 1.5 |
| | 0 | 0.6 | 1.00 | |

The ratios of 5,6,7,8-tetrahydronaphthalen-1-ol to (4S)-(4-(prop-1-en-2-yl)cyclohex-1-enyl)methanol tested imaged from 1/0.025 to 1/400. The synergistic ratios of 5,6,7,8-tetrahydronaphthalen-1-ol to (4S)-(4-(prop-1-en-2-yl)cyclohex-1-enyl)methanol range from 1/0.15 to 1/10.

TABLE 12

First Component (A) = 5,6,7,8-tetrahydronaphthalen-2-ol
Second Component (B) = (4S)-(4-(prop-1-en-2-yl)cyclohex-1-enyl)methanol

| Microorganism | $Q_a$ | $Q_b$ | SI | Ratio A to B |
|---|---|---|---|---|
| E. coli 10536 | 0.6 | 0 | 1.00 | |
| | 0.3 | 0.075 | 0.63 | 1 to 0.25 |
| | 0.4 | 0.075 | 0.79 | 1 to 0.19 |
| | 0.5 | 0.075 | 0.96 | 1 to 0.15 |
| | 0.3 | 0.1 | 0.67 | 1 to 0.33 |
| | 0.4 | 0.1 | 0.83 | 1 to 0.25 |
| | 0.06 | 0.3 | 0.60 | 1 to 5 |
| | 0.08 | 0.3 | 0.63 | 1 to 3.75 |
| | 0.1 | 0.3 | 0.67 | 1 to 3 |
| | 0.2 | 0.3 | 0.83 | 1 to 1.5 |
| | 0 | 0.6 | 1.00 | |

The ratios of 5,6,7,8-tetrahydronaphthalen-2-ol to (4S)-(4-(prop-1-en-2-yl)cyclohex-1-enyl)methanol tested ranged from 1/0.025 to 1/400. The synergistic ratios of 5,6,7,8-tetrahydronaphthalen-2-ol to (4S)-(4-(prop-1-en-2-yl)cyclohex-1-enyl)methanol range from 1/0.15 to 1/5.

TABLE 13

First Component (A) = 5,6,7,8-tetrahydronaphthalen-1-ol
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 0.6 | 0 | 1.00 | |
| | 0.5 | 0.075 | 0.96 | 1 to 0.15 |
| | 0.3 | 0.1 | 0.67 | 1 to 0.33 |
| | 0.4 | 0.1 | 0.83 | 1 to 0.25 |
| | 0.06 | 0.3 | 0.60 | 1 to 5 |
| | 0.08 | 0.3 | 0.63 | 1 to 3.75 |
| | 0.1 | 0.3 | 0.67 | 1 to 3 |
| | 0.2 | 0.3 | 0.83 | 1 to 1.5 |
| | 0 | 0.6 | 1.00 | |

The ratios of 5,6,7,8-tetrahydronaphthalen-1-ol to 2,4,6-trimethyl-3-cyclohexene-1-methanol tested ranged from 1/0.025 to 1/400. The synergistic ratios of 5,6,7,8-tetrahydronaphthalen-1-ol to 2,4,6-trimethyl-3-cyclohexene-1-methanol range from 1/0.15 to 1/5.

TABLE 14

First Component (A) = 5,6,7,8-tetrahydronaphthalen-2-ol
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 0.8 | 0 | 1.00 | |
| | 0.6 | 0.025 | 0.79 | 1 to 0.04 |
| | 0.6 | 0.05 | 0.83 | 1 to 0.08 |
| | 0.3 | 0.075 | 0.50 | 1 to 0.25 |
| | 0.4 | 0.075 | 0.63 | 1 to 0.19 |
| | 0.5 | 0.075 | 0.75 | 1 to 0.15 |
| | 0.6 | 0.075 | 0.88 | 1 to 0.13 |
| | 0.3 | 0.1 | 0.54 | 1 to 0.33 |
| | 0.4 | 0.1 | 0.67 | 1 to 0.25 |
| | 0.5 | 0.1 | 0.79 | 1 to 0.20 |
| | 0.6 | 0.1 | 0.92 | 1 to 0.17 |
| | 0.03 | 0.30 | 0.54 | 1 to 10 |
| | 0.04 | 0.30 | 0.55 | 1 to 7.5 |
| | 0.05 | 0.30 | 0.56 | 1 to 6 |
| | 0.06 | 0.30 | 0.58 | 1 to 5 |
| | 0.08 | 0.30 | 0.60 | 1 to 3.75 |
| | 0.1 | 0.30 | 0.63 | 1 to 3 |
| | 0.2 | 0.30 | 0.75 | 1 to 1.5 |
| | 0.3 | 0.30 | 0.88 | 1 to 1 |
| | 0 | 0.6 | 1.00 | |

The ratios of 5,6,7,8-tetrahydronaphthalen-2-ol to 2,4,6-trimethyl-3-cyclohexene-1-methanol tested ranged from 1/0.025 to 1/400. The synergistic ratios of 5,6,7,8-tetrahydronaphthalen-2-ol to 2,4,6-trimethyl-3-cyclohexene-1-methanol range from 1/0.04 to 1/10.

TABLE 15

First Component (A) = 2-cyclopentylphenol
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.3 | 0 | 1.00 | |
| | 0.2 | 0.05 | 0.83 | 1 to 0.25 |
| | 0.2 | 0.1 | 1.00 | 1 to 0.5 |
| | 0.08 | 0.2 | 0.93 | 1 to 2.5 |
| | 0 | 0.3 | 1.00 | |

The ratios of 2-cyclopentylphenol to 2-(4-methylcyclohex-3-enyl)propan-1-ol tested ranged from 1/0.025 to 1/250. The synergistic ratios of 2-cyclopentylphenol to 2-(4-methylcyclohex-3-enyl)propan-1-ol range from 1/0.25 to 1/2.5.

TABLE 16

First Component (A) = 4-cyclopentylphenol
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 0.3 | 0 | 1.00 | |
| | 0.2 | 0.025 | 0.75 | 1 to 0.13 |
| | 0.2 | 0.075 | 0.92 | 1 to 0.38 |
| | 0.1 | 0.1 | 0.67 | 1 to 1 |
| | 0.06 | 0.2 | 0.87 | 1 to 3.33 |
| | 0.08 | 0.2 | 0.93 | 1 to 2.5 |
| | 0 | 0.3 | 1.00 | |

The ratios of 4-cyclopentylphenol to 2-(4-methylcyclohex-3-enyl)propan-1-ol tested ranged from 1/0.025 to 1/250. The synergistic ratios of 4-cyclopentylphenol to 2-(4-methylcyclohex-3-enyl)propan-1-ol range from 1/0.13 to 1/3.33.

TABLE 17

First Component (A) = 2-cyclopentylphenol
Second Component (B) = (4-(prop-1-en-2-yl)cyclohex-1-enyl)methanol

| Microorganism | $Q_a$ | $Q_b$ | SI | Ratio A to B |
|---|---|---|---|---|
| E. coli 10536 | 0.3 | 0 | 1.00 | |
| | 0.2 | 0.075 | 0.82 | 1 to 0.38 |
| | 0.2 | 0.1 | 0.87 | 1 to 0.5 |
| | 0.1 | 0.2 | 0.73 | 1 to 2 |
| | 0.006 | 0.3 | 0.62 | 1 to 50 |
| | 0.008 | 0.3 | 0.63 | 1 to 37.5 |
| | 0.01 | 0.3 | 0.63 | 1 to 30 |
| | 0.02 | 0.3 | 0.67 | 1 to 15 |
| | 0.03 | 0.3 | 0.70 | 1 to 10 |
| | 0.05 | 0.3 | 0.77 | 1 to 6 |
| | 0.06 | 0.3 | 0.80 | 1 to 5 |
| | 0.08 | 0.3 | 0.87 | 1 to 3.75 |
| | 0.1 | 0.3 | 0.93 | 1 to 3 |
| | 0 | 0.5 | 1.00 | |

The ratios of 2-cyclopentylphenol to (4-(prop-1-en-2-yl)cyclohex-1-enyl)methanol tested ranged from 1/0.025 to 1/250. The synergistic ratios of 2-cyclopentylphenol to (4-(prop-1-en-2-yl)cyclohex-1-enyl)methanol range from 1/0.38 to 1/50.

TABLE 18

First Component (A) = 4-cyclopentylphenol
Second Component (B) = (4-(prop-1-en-2-yl)cyclohex-1-enyl)methanol

| Microorganism | $Q_a$ | $Q_b$ | SI | Ratio A to B |
|---|---|---|---|---|
| E. coli 10536 | 0.5 | 0 | 1.00 | |
| | 0.4 | 0.025 | 0.88 | 1 to 0.06 |
| | 0.2 | 0.075 | 0.65 | 1 to 0.38 |
| | 0.3 | 0.075 | 0.85 | 1 to 0.25 |
| | 0.2 | 0.1 | 0.73 | 1 to 0.5 |
| | 0.3 | 0.1 | 0.93 | 1 to 0.33 |
| | 0.08 | 0.2 | 0.83 | 1 to 2.5 |
| | 0.1 | 0.2 | 0.87 | 1 to 2 |
| | 0 | 0.3 | 1.00 | |

The ratios of 4-cyclopentylphenol to (4-(prop-1-en-2-yl)cyclohex-1-enyl)methanol tested ranged from 1/0.025 to 1/250. The synergistic ratios of 4-cyclopentylphenol to (4-(prop-1-en-2-yl)cyclohex-1-enyl)methanol range from 1/0.06 to 1/2.5.

TABLE 19

First Component (A) = 2-cyclopentylphenol
Second Component (B) = 2,4,6-trimethyl-3-cyclohexene-1-methanol

| Microorganism | $Q_a$ | $Q_b$ | SI | Ratio A to B |
|---|---|---|---|---|
| E. coil 10536 | 0.5 | 0 | 1.00 | |
| | 0.2 | 0.025 | 0.44 | 1 to 0.13 |
| | 0.3 | 0.025 | 0.64 | 1 to 0.08 |
| | 0.4 | 0.025 | 0.84 | 1 to 0.06 |
| | 0.3 | 0.05 | 0.68 | 1 to 0.17 |
| | 0.4 | 0.05 | 0.88 | 1 to 0.13 |
| | 0.2 | 0.075 | 0.53 | 1 to 0.38 |
| | 0.3 | 0.075 | 0.73 | 1 to 0.25 |
| | 0.4 | 0.075 | 0.93 | 1 to 0.19 |
| | 0.2 | 0.1 | 0.57 | 1 to 0.5 |
| | 0.3 | 0.1 | 0.77 | 1 to 0.33 |
| | 0.4 | 0.1 | 0.97 | 1 to 0.25 |
| | 0.1 | 0.3 | 0.70 | 1 to 3 |
| | 0.2 | 0.3 | 0.90 | 1 to 1.5 |
| | 0 | 0.6 | 1.00 | |

The ratios of 2-cyclopentylphenol to 2,4,6-trimethyl-3-cyclohexene-1-methanol tested ranged from 1/0.025 to 1/400. The synergistic ratios of 2-cyclopentylphenol to 2,4,6-trimethyl-3-cyclohexene-1-methanol range from 1/0.06 to 1/3.

TABLE 20

First Component (A) = 4-cyclopentylphenol
Second Component (B) = 2,4,6-trimethyl-3-cyclohexene-1-methanol

| Microorganism | $Q_a$ | $Q_b$ | SI | Ratio A to B |
|---|---|---|---|---|
| E. coil 10536 | 0.2 | 0 | 1.00 | |
| | 0.1 | 0.05 | 0.67 | 1 to 0.5 |
| | 0.1 | 0.075 | 0.75 | 1 to 0.75 |
| | 0.08 | 0.1 | 0.73 | 1 to 1.25 |
| | 0.1 | 0.1 | 0.83 | 1 to 1 |
| | 0 | 0.3 | 1.00 | |

The ratios of 4-cyclopentylphenol to 2,4,6-trimethyl-3-cyclohexene-1-methanol tested ranged from 1/0.025 to 1/400. The synergistic ratios of 4-cyclopentylphenol to 2,4,6-trimethyl-3-cyclohexene-1-methanol range from 1/0.5 to 1/1.25.

TABLE 21

First Component (A) = 3-isopropyl-6-methylbenzene-1,2-diol
Second Component (B) = 2-(4-methylcylohex-3-enyl)propan-1-ol

| Microorganism | $Q_a$ | $Q_b$ | SI | Ratio A to B |
|---|---|---|---|---|
| E. coli 10536 | 1.0 | 0 | 1.00 | |
| | 0.8 | 0.025 | 0.90 | 1 to 0.03 |
| | 0.8 | 0.05 | 1.00 | 1 to 0.06 |
| | 0.6 | 0.075 | 0.90 | 1 to 0.13 |
| | 0.6 | 0.1 | 1.00 | 1 to 0.17 |
| | 0 | 0.25 | 1.00 | |

The ratios of 3-isopropyl-6-methylbenzene-1,2-diol to 2-(4-methylcyclohex-3-enyl)propan-1-ol tested ranged from 1/0.025 to 1/350. The synergistic ratios of 3-isopropyl-6-methylbenzene-1,2-diol to 2-(4-methylcyclohex-3-enyl)propan-1-ol range from 1/0.03 to 1/0.13.

TABLE 22

First Component (A) = 4-tert-butylbenzene-1,2-diol
Second Component (B) = 2-(4-methylcyclohex-3-enyl)propan-1-ol

| Microorganism | $Q_a$ | $Q_b$ | SI | Ratio A to B |
|---|---|---|---|---|
| E. coli 10536 | 1.00 | 0 | 1.00 | |
| | 0.8 | 0.05 | 1.00 | 1 to 0.06 |
| | 0.6 | 0.075 | 0.90 | 1 to 0.13 |

TABLE 22-continued

First Component (A) = 4-tert-butylbenzene-1,2-diol
Second Component (B) = 2-(4-methylcyclohex-3-enyl)propan-1-ol

| Microorganism | $Q_a$ | $Q_b$ | SI | Ratio A to B |
|---|---|---|---|---|
| | 0.6 | 0.1 | 1.00 | 1 to 0.17 |
| | 0 | 0.25 | 1.00 | |

The ratios of 4-tert-butylbenzene-1,2-diol to 2-(4-methylcyclohex-3-enyl)propan-1-ol tested ranged from 1/0.025 to 1/350. The synergistic ratios of 4-tert-butylbenzene-1,2-diol to 2-(4-methylcyclohex-3-enyl)propan-1-ol is 1/0.13.

TABLE 23

First Component (A) = 3-isopropyl-6-methylbenzene-1,2-diol
Second Component (B) = (4S)-(4-(prop-1-en-2-yl)cyclohex-1-enyl)methanol

| Microorganism | $Q_a$ | $Q_b$ | SI | Ratio A to B |
|---|---|---|---|---|
| E. coli 10536 | 0.8 | 0 | 1.00 | |
| | 0.6 | 0.075 | 0.88 | 1 to 0.13 |
| | 0.6 | 0.1 | 0.92 | 1 to 0.17 |
| | 0.002 | 0.3 | 0.50 | 1 to 150 |
| | 0.004 | 0.3 | 0.51 | 1 to 75 |
| | 0.006 | 0.3 | 0.51 | 1 to 50 |
| | 0.01 | 0.3 | 0.51 | 1 to 30 |
| | 0.02 | 0.3 | 0.53 | 1 to 15 |
| | 0.06 | 0.3 | 0.58 | 1 to 5 |
| | 0.1 | 0.3 | 0.63 | 1 to 3 |
| | 0.2 | 0.3 | 0.75 | 1 to 1.5 |
| | 0.3 | 0.3 | 0.88 | 1 to 1 |
| | 0 | 0.6 | 1.00 | |

The ratios of 3-isopropyl-6-methylbenzene-1,2-diol to (4S)-(4-prop-1-en-2-yl)cyclohex-1-enyl)methanol tested ranged from 1/0.025 to 1/400. The synergistic ratios of 3-isopropyl-6-methylbenzene-1,2-diol to (4S)-(4-(prop-1-en-2-yl)cyclohex-1-enyl)methanol range from 1/0.13 to 1/150.

TABLE 24

First Component (A) = 4-tert-butylbenzene-1,2-diol
Second Component (B) = (4S)-(4-(prop-1-en-2-yl)cyclohex-1-enyl)methanol

| Microorganism | $Q_a$ | $Q_b$ | SI | Ratio A to B |
|---|---|---|---|---|
| E. coli 10536 | 1.0 | 0 | 1.00 | |
| | 0.8 | 0.025 | 0.88 | 1 to 0.03 |
| | 0.8 | 0.05 | 0.97 | 1 to 0.06 |
| | 0.6 | 0.075 | 0.85 | 1 to 0.13 |
| | 0.6 | 0.1 | 0.93 | 1 to 0.17 |
| | 0 | 0.3 | 1.00 | |

The ratios of 4-tert-butylbenzene-1,2-diol to (4S)-(4-(prop-1-en-2-yl)cyclohex-1-enyl)methanol tested ranged from 1/0.025 to 1/400. The synergistic ratios of 4-tert-butylbenzene-1,2-diol to (4S)-(4-(prop-1-en-2-yl)cyclohex-1-enyl)methanol range from 1/0.03 to 1/0.17.

TABLE 25

First Component (A) = 3-isopronyl-6-methylbenzene-1,2-diol
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 0.8 | 0 | 1.00 | |
| | 0.6 | 0.05 | 0.83 | 1 to 0.08 |
| | 0.6 | 0.075 | 0.88 | 1 to 0.13 |

TABLE 25-continued

First Component (A) = 3-isopronyl-6-methylbenzene-1,2-diol
Second Component (B) = 2,4,6-trimethyl-3-cyclohexene-1-methanol

| Microorganism | $Q_a$ | $Q_b$ | SI | Ratio A to B |
|---|---|---|---|---|
| | 0.6 | 0.1 | 0.92 | 1 to 0.17 |
| | 0.004 | 0.3 | 0.51 | 1 to 75 |
| | 0.008 | 0.3 | 0.51 | 1 to 37.5 |
| | 0.01 | 0.3 | 0.51 | 1 to 30 |
| | 0.04 | 0.3 | 0.55 | 1 to 7.5 |
| | 0.06 | 0.3 | 0.58 | 1 to 5 |
| | 0.1 | 0.3 | 0.63 | 1 to 3 |
| | 0.2 | 0.3 | 0.75 | 1 to 1.5 |
| | 0.3 | 0.3 | 0.88 | 1 to 1 |
| | 0 | 0.6 | 1.00 | |

The ratios of 3-isopropyl-6-methylbenzene-1,2-diol to 2,4,6-trimethyl-3-cyclohexene-1-methanol tested ranged from 1/0.025 to 1/400. The synergistic ratios of 3-isopropyl-6-methylbenzene-1,2-diol to 2,4,6-trimethyl-3-cyclohexene-1-methanol range from 1/0.08 to 1/75.

TABLE 26

First Component (A) = 4-tert-butylbenzene-1,2-diol
Second Component (B) = 2,4,6-trimethyl-3-cyclohexene-1-methanol

| Microorganism | $Q_a$ | $Q_b$ | SI | Ratio A to B |
|---|---|---|---|---|
| E. coli 10536 | 1.0 | 0 | 1.00 | |
| | 0.6 | 0.025 | 0.64 | 1 to 0.04 |
| | 0.8 | 0.025 | 0.84 | 1 to 0.03 |
| | 0.8 | 0.05 | 0.88 | 1 to 0.06 |
| | 0.8 | 0.075 | 0.93 | 1 to 0.09 |
| | 0.8 | 0.1 | 0.97 | 1 to 0.13 |
| | 0.08 | 0.3 | 0.58 | 1 to 3.75 |
| | 0.1 | 0.3 | 0.60 | 1 to 3 |
| | 0.2 | 0.3 | 0.70 | 1 to 1.5 |
| | 0.3 | 0.3 | 0.80 | 1 to 1 |
| | 0.4 | 0.3 | 0.90 | 1 to 0.75 |
| | 0 | 0.6 | 1.00 | |

The ratios of 4-tert-butylbenzene-1,2-diol to 2,4,6-trimethyl-3-cyclohexene-1-methanol tested ranged from 1/0.025 to 1/400. The synergistic ratios of 4-tert-butylbenzene-1,2-diol to 2,4,6-trimethyl-3-cyclohexene-1-methanol range from 1/0.03 to 1/3.75.

The following microbicidal compositions were tested and were found not to be synergistic; 3-isopropyl-5-methylphenol and 2-methyl-5-(prop-1-en-2-yl)cyclohexanol tested at a weight ratio of 1/0.025 to 1/350; 4-isopropyl-3-methylphenol and 2-methyl-5-(prop-1-en-2-yl)cyclohexanol tested at a weight ratio of 1/0.025 to 1/350; 2-tert-butyl-5-methylphenol and 2-methyl-5-(prop-1-en-2-yl)cyclohexanol tested at a weight ratio of 1/0.025 to 1/350; 2-sec-butylphenol and 2-methyl-5-(prop-1-en-2-yl)cyclohexanol tested at a weight ratio of 1/0.025 to 1/350; 4-n-butylphenol and 2-methyl-5-(prop-1-en-2-yl)cyclohexanol tested at a weight ratio of 1/0.025 to 1/350; 4-pentylphenol and 2-methyl-5-(prop-1-en-2-yl)cyclohexanol tested at a weight ratio of 1/0.025 to 1/350; 3-isopropyl-5-methylphenol and (1R,2S,5R)-5-methyl-2-(prop-1-en-2-yl)cyclohexanol tested at a weight ratio of 1/0.025 to 1/3-50; 2-tert-butyl-5-methylphenol and (1R,2S,5R)-5-methyl-2-(prop-1-en-2-yl)cyclohexanol tested at a weight ratio of 1/0.025 to 1/350; 4-pentylphenol and (1R,2S,5R)-5-methyl-2-(prop-1-en-2-yl)cyclohexanol tested at a weight ratio of 1/0.025 to 1/350; 3-n-propylphenol and (1S,2S,5R)-2-isopropyl-5-methylcyclohexyl acetate tested at a weight ratio of 1/0.025 to 1/1100; 2-n-propylphenol and 2-(4-methylcyclohex-3-enyl)propan-2-yl propionate tested at a weight ratio of 1/0.025 to 1/1100; 3-n-propylphenol and 2-(4-methylcyclohex-3-enyl)propan-2-yl propionate tested, at a weight ratio of 1/0.025 to 1/11.00; 4-n-butylphenol and 2-(4-methylcyclohex-3-enyl)propan-2-yl propionate tested at a weight ratio of 1/0.025 to 1/1100; 3-n-propylphenol and 2-(4-methylcyclohex-3-enyl)propan-2-yl butyrate tested at a weight ratio of 1/0.025 to 1/1100; 4-n-butylphenol and 2-(4-methylcyclohex-3-enyl)propan-2-yl butyrate tested at a weight ratio of 1/0.025 to 1/1100; 2-sec-butylphenol and 2-(4-methylcyclohex-3-enyl)propan-1-ol tested at a weight ratio of 1/0.025 to 1/250; 4-pentylphenol and 2-(4-methylcyclohex-3-enyl)propan-1-ol tested at a weight ratio of 1/0.025 to 1/250; 2-sec-butylphenol and 2,4,6-trimethyl-3-cyclohexene-1-methanol tested at a weight ratio of 1/0.025 to 1/400; 2-tert-butylphenol and 3,7-dimethylocta-1,6-dien-3-ol tested at a weight ratio of 1/0.025 to 3/350; 2-sec-butylphenol and 3,7-dimethylocta-1,6-dien-3-ol tested at a weight ratio of 1/0.025 to 1/350; 4-sec-butylphenol and 3,7-dimethylocta-1,6-dien-3-ol tested at a weight ratio of 1/0.025 to 1/350; 4-sec-butylphenol and (E)-3,7-dimethylocta-2,6-dien-1-ol tested at a weight ratio of 1/0.025 to 1/300; 4-chloro-2-isopropyl-5-methylphenol and 5-methyl-2-(prop-1-en-2-yl)cyclohexanol tested at a weight ratio of 1/0.025 to 1/350; 4-chloro-2-isopropyl-5-methylphenol and 2-methyl-5-(prop-1-en-2-yl)cyclohex-2-enol tested at a weight ratio of 1/0.025 to 1/450; 4-chloro-2-isopropyl-5-methylphenol and 2-(4-methylcyclohex-3-enyl)propan-1-ol tested at a weight ratio of 1/0.025 to 1/250; 4-chloro-2-isopropyl-5-methylphenol and (4S)-(4-(prop-1-en-2-yl)cyclohex-1-enyl)methanol tested at a weight ratio: of 1/0.025 to 1/250; 4-chloro-2-isopropyl-5-methylphenol and 2,4,6-trimethyl-3-cyclohexene-1-methanol tested at a weight ratio of 1/0.025 to 1/400; 4-chloro-2-isopropyl-5-methylphenol and 3,7-dimethylocta-1,6-dien-3-ol tested at a weight ratio of 1/0.025 to 1/250; 4-chloro-2-isopropyl-5-methylphenol and (E)-3,7-dimethylocta-2,6-dien-1-ol tested at a weight ratio of 1/0.025 to 1/250; 4-chloro-2-isopropyl-5-methylphenol and cis-3,7-dimethyl-2,6-octadien-1-ol tested at a weight ratio of 1/0.025 to 1/350; 2-hydroxydiphenylmethane and 2-((1s,4r)-4-propylcyclohexyl)propane-1,3-diol tested at a weight ratio of 1/0.025 to 1/1100; 2-hydroxydiphenylmethane and (1S,2S,5R)-2-isopropyl-5-methylcyclohexyl acetate tested at a weight ratio of 1/0.025 to 1/1100; 2-hydroxydiphenylmethane and 2-(4-methylcyclohex-3-enyl)propan-2-yl propionate tested at a weight ratio of 1/0.025 to 1/1100; 2-hydroxydiphenylmethane and 2-(4-methylcyclohex-3-enyl)propan-2-yl butyrate tested at a weight ratio of 1/0.025 to 1/1100; 4-hydroxydiphenylmethane and (4S)-(4-(prop-1-en-2-yl)cyclohex-1-enyl)methanol tested at a weight ratio of 1/0.025 to 1/400; 5,6,7,8-tetrahydronaphthalen-1-ol and (1S,2S,5R)-2-isopropyl-5-methylcyclohexyl acetate tested at a weight ratio of 1/0.025 to 1/1100; 5,6,7,8-tetrahydronaphthalen-2-ol and (1S,2S,5R)-2-isopropyl-5-methylcyclohexyl acetate tested at a weight ratio of 1/0.025 to 1/1100; 5,6,7,8-tetrahydronaphthalen-1-ol and 2-(4-methylcyclohex-3-enyl)propan-2-yl propionate tested at a weight ratio of 1/0.025 to 1/1100; 5,6,7,8-tetrahydronaphthalen-2-ol and 2-(4-methylcyclohex-3-enyl)propan-2-yl propionate tested at a weight ratio of 1/0.025 to 1/1100; 5,6,7,8-tetrahydronaphthalen-1-ol and 2-(4-methylcyclohex-3-enyl)propan-2-yl butyrate tested at a weight ratio of 1/0.025 to 1/1100; 5,6,7,8-tetrahydronaphthalen-2-ol and 2-(4-methylcyclohex-3-enyl)propan-2-yl butyrate tested at a weight ratio of 1/0.025 to 1/1100; 2-cyclopentylphenol and 2-methyl-5-(prop-1-en-2-yl)cyclohexanol tested at a weight ratio of 1/0.025 to 1/350; and 4-pentylphenol and (4S)-(4-(prop-1-en-2-yl)cyclohex-1-enyl)methano tested at a weight ratio of 1/0.025 to 1/250.

Further experiments were carried out with the two class of actives that have been claimed as acting synergistically in providing antimicrobial activity. The common names of the compounds used are given below:

(4S)-(4-(prop-1-en-2-yl)cyclohex-1-enyl)methanol: (S)-(−)-perillyl alcohol.
2,4,6-trimethyl-3-cyclohexene-1-methanol iso-cyclogeraniol.
Trans-4,6-dimethyl-3-Cyclohexene-1-methanol; floralol
2,4-Dimethylcyclohexylmethanol; dihydrofloralol
4-chloro-3,5-dimethylphenol
4-chloro-2-isopropyl-5-methylphenol
2-hydroxydiphenylmethane
4-hydroxydiphenylmethane
5,6,7,8-tetrahydronaphthalen-1-ol
5,6,7,8-tetrahydronaphthalen-2-ol
2-cyclopentylphenol
4-cyclopentylphenol
3-isopropyl-6-methylbenzene-1,2-diol
4-tert-butylbenzene-1,2-diol
15 Second Contact Kill Test Versus *E. Coli* and *S. Aureus*
Experimental Method
Antimicrobial efficacy is tested against a representative pathogenic bacterial organism, Gram negative *Escherichia coli*. Concentrations of actives are expressed in terms of the percentage weight/volume (% w/v) throughout Example 1. Selected materials were also tested against a representative Grant positive *Staphylococcus aureus*.
*E. coli* Bacterial Stock
An overnight culture of *Escherichia coli* (10536 strain) was prepared in 50 ml total volume of TSB broth, grown for ca. 18 hrs at 37° C. and shaken at 150 rpm. 1 ml of this overnight *E. coli* culture was transferred to 50 ml of fresh TSB broth and incubated at 37° C. at 150 rpm for ca. 4 hours. This culture was separated into equal volumes and centrifuged at 4000 rpm for 15 minutes, washed with sterile saline (0.85% NaCl), centrifuged once more and re-suspended in saline to give a final concentration of 0.8 $OD_{620}$ equivalent to about $10^8$ cells per milliliter for this particular organism. Here, $OD_{620}$ indicates the absorbance of a sample in a cuvette of 1.0 cm path length at a wavelength of 620 nm. This bacterial stock was used for assaying against antimicrobial actives (in triplicate).
*S. Aureus* Bacterial Stock
An overnight culture of *Staphylococcus aureus* (10788 strain) was inoculated onto a Tripticase Soy Agar (TSA) plate and grown for ca. 18 hrs at 37° C. The culture *S. aureus* was washed from the plate using sterile saline (0.85% NaCl) solution and a sterile spreader and suspended in 50 ml saline. This suspension was separated into equal volumes and centrifuged at 4000 rpm for 15 minutes. Following centrifugation the pellet was re-suspended in saline to give a final concentration of 0.35 $OD_{620}$ equivalent to about $10^8$ cells per milliliter for this particular organism. Here, $OD_{620}$ indicates the absorbance of a sample in a cuvette of 1.0 cm path length at a wavelength of 620 nm. This bacterial stock was used for assaying against antimicrobial actives (in triplicate).
Protocol
The following assay describes the testing of 8 materials using 6 dilutions across half of a 96-well micro titre plate (MTP). Using this approach it is possible to assay 16 actives (without replicates) with one full dilution plate, replicating this set up in two halves of the plate columns, 1-6 and 7-12.

1M solutions of the test actives were prepared in dimethylsulphoxide (DMSO). Stock solutions of the actives at 11.1 times the desired final concentration were prepared by diluting the DMSO solutions in water, so that for example a 0.89% w/v solution, was prepared for a desired "in test" concentration of 0.8% w/v in order to allow for the further dilution, of the active when the bacterial suspension is added (dilution from 270 μl to 300 μl), as described below.
Aliquots (270 μl) of the materials at 1.11 times the final concentration were dispensed into the wells of the MTP along one column (A1-H1). This MTP was labelled as the "Screening plate".
In another MTP, labelled as the "Dilution plate", 27 μl of D/E neutralising solution from DIFCO Composition was added to column 1. The composition of the neutralising solution was as follows: pancreatic digest of casein, 5.0 g/L; Yeast Extract, 2.5 g/L; Dextrose, 10 g/L, sodium thioglycollate, 1.0 g/L, sodium thiosulphate, 6.0 g/L; sodium bisulphite, 2.5 g/L; Polysorbate 80, 5.0 g/L; lecithin 7.0 g/L; bromocresol purple, 0.02 g/L with a pH in the range 7.6±0.2.
270 μl of tryptone diluent solution was added to all the remaining wells of the Dilution MTP (columns 2-6).
Bacterial stock (30 μl) was then added to the prepared 270 μl of the solution of actives in the Screening Plate and mixed, using a multichannel pipette with 8 tips to aspirate and dispense the same volume of bacterial stock in parallel to 8 wells in rows A-H. After a contact time of 15 seconds, the mixtures were quenched by transferring 30 μl volumes of the mixtures into the 270 μl D/E neutralising solution in the prepared dilution plate, using aspiration to mix. After exactly 5 minutes in the D/E neutralising solution, 30 μl volumes were transferred from column 1 to column 2 of the Dilution MTP and mixed, before transferring further 30 μl volumes from column 2 into column 3. This process was repeated serially diluting the bacteria across the plate to column 6.
30 μl volumes from each well in the Dilution MTP were transferred onto pre-labelled segment of Tryptone Soya Agar (TSA) plates starting from the lowest bacterial concentration (highest dilution, column 6) to the highest bacterial concentration (column 1). The TSA plates were allowed to stand for ca. 2 hours so that the 30 μl inocula spots could dry and the plates were then inverted and incubated overnight at 37° C. before enumerating the bacterial colonies at the labelled dilutions to determine the effects of the actives on bacterial growth.
Calculation of Results
Mean bacterial survival numbers $N_{MBS}$ (expressed in Log CFU/ml) are obtained by first determining the segment of the TSA plate where the number of bacterial colonies is countable. From the colony number in this segment, $N_{MBS}$ is calculated by the formula:

$$N_{MBS} = \log \{N_{col} \cdot 10^{DF} \cdot 100/3\}$$

Here, $N_{col}$ is the colony count, and DF is the dilution factor taken from the MTP-well corresponding to the TSA plate segment (i.e. DF may range from 1 for the quench, to 6 for the highest dilution). The factor 100/3 is a conversion factor from the volume of the inocula spot to one milliliter.
Every assay test was performed in triplicate. The reported mean bacterial survival results are the average of such a triplet, the error is the corresponding standard deviation.

Thus, a value of $N_{MBS}$ of about 7 corresponds to a count of about 3 colonies from the fifth dilution well, i.e. with DF=5. Such a count of about 7 is generally observed when bacteria are exposed to non-biocidal materials. In case no surviving colonies are observed in any segment of the TSA plate, this is interpreted as complete kill and a value of $N_{MBS}=0$ is reported.

TABLE 26

Antibacterial activities of thymol, and mono-substituted phenols alone and in combination with terpineol against *E. Coli*

| Phenolic compound concentration (% w/v) | Antimicrobial alcohol (% w/v) | $N_{MBS}$ [log CFU/ml] | Standard deviation |
|---|---|---|---|
| 0 | 0.4% floralol | 0 | 0 |
| 0 | 0.15% floralol | 7.92 | 0.06 |
| 0 | 0.5% dihydrofloralol | 0.00 | 0.00 |
| 0 | 0.3% dihydrofloralol | 6.18 | 0.22 |
| 0.05% 4-benzylphenol | 0 | 0.00 | 0.00 |
| 0.025% 4-benzylphenol | 0 | 4.20 | 0.35 |
| 0.0125% 4-benzylphenol | 0 | 7.75 | 0.09 |
| 0.05% 4-benzylphenol | 0.1% floralol | 0.00 | 0.00 |
| 0.025% 4-benzylphenol | 0.1% floralol | 0.00 | 0.00 |
| 0.0125% 4-benzylphenol | 0.1% floralol | 5.00 | 0.21 |
| 0.05% 4-benzylphenol | 0.12% dihydrofloralol | 0.00 | 0.00 |
| 0.025% 4-benzylphenol | 0.12% dihydrofloralol | 0.00 | 0.00 |
| 0.0125% 4-benzylphenol | 0.12% dihydrofloralol | 0.00 | 0.00 |
| 0.0075% 4-benzylphenol | 0.12% dihydrofloralol | 7.48 | 0.12 |

TABLE 27

Minimum biocidal concentration of antimicrobial components

| Component | MBC (% w/v) |
|---|---|
| 4-benzylphenol | 0.05 |
| floralol | 0.3 |
| dihydrofloralol | 0.5 |

TABLE 28

Extent of synergistic interactions between binary compound mixtures for compositions providing complete bacterial kill against *E. Coli*

| Phenolic compound | | Antimicrobial alcohol | | | | |
|---|---|---|---|---|---|---|
| | MBC % (w/v) | $FBC^a$ | | MBC % (w/v) | $FBC^b$ | $\Sigma FBC$ | Evidence of Synergy$^c$ |
| 4-benzylphenol | 0.5 | 0.5 | Floralol | 0.3 | 0.33 | 0.83 | Yes |
| 4-benzylphenol | 0.5 | 0.5 | Dihydrofloralol | 0.5 | 0.24 | 0.74 | Yes |
| 4-benzylphenol | 0.5 | 0.25 | Dihydrofloralol | 0.5 | 0.24 | 0.49 | Yes |

Test Methodology for Automated Assessment of Efficacy in Surfactant Base

Microbiocidal Activity of Actives as Per the Invention in a Model Surfactant Medium Test Methodology for Automated Assessment of Efficacy in Surfactant Base In these examples, the efficacy of combinations of actives were tested in a surfactant cleansing formulation comprising 2.85% sodium cocoyl glycinate and 1.85% sodium lauroamphoacetate.

This corresponds to a 50% in use dilution with water of a neat formulation containing 5.7% cocoyl glycinate and 37% % sodium, lauroamphoacetate during hand washing.

Solutions were prepared such that the concentrations of the surfactant components and test actives were 1.1× the final desired concentration in order to allow for dilution with the bacterial inoculum in the test. The solutions were manually adjusted to pH 10.0 by dropwise addition of sodium hydroxide solution, as measured with a pH meter at ambient temperature.

The efficacy of the combinations of the present invention was determined against *Escherichia coli* (*E. coli*—ATCC #10536), at a concentration of approximately $1 \times 10^8$ bacteria per mL.

Tests were conducted using standard microtiter plate assays using an automated liquid handling system. 270 µl of the surfactant test solution was pipetted into each well of the microtitre plate and 30 µl of the bacterial suspension was then added. Alter exactly 15 seconds of bacterial exposure, a 30 µl volume of bacterial cells was withdrawn and transferred to 270 µl of D/E quench solution. After 5 minutes in the D/E quench, the optical density (OD) was measured for each plate in turn at two specific wavelengths (450 nm and 590 nm). These provide a dual check of antimicrobial activity, as the $OD_{450}$ reading is specific for the yellow colour of D/E quench when bacterial growth is observed, whereas $OD_{590}$ is specific for the initial purple colour of the D/E quench which is retained if no bacterial growth is observed. After the time zero OD measurements, plates were then incubated at 37° C. overnight (16 hours) before repeating the OD measurements. Delta OD values were calculated by subtracting the OD values at 16 hours from the initial value at time zero. Bacterial growth is observed as an increase in $OD_{450}$ and a decrease in $\Delta OD_{590}$. To identify antibacterially efficacious systems (those preventing appreciable bacterial growth after incubation), the following threshold changes in OD readings have been adopted: if (1). $OD_{450}$ increases by less than 0.2 absorbance unit on incubation and (2). $OD_{590}$ decreases by less than 0.35 unit on incubation. Conversely, where $OD_{450}$ increases by more than 0.2 AU and $OD_{590}$ decreases by more than 0.35 unit after incubation, corresponding to a colour shift from purple to yellow, the test system allows bacterial growth and is not deemed efficacious. Four replicate measurements in the same plate have been made for each test system. The number of replicate wells showing either bacterial growth or no growth is also readily assessed by eye by following the colour change.

Dose responses for individual components and binary mixtures of actives at a fixed concentration ratio were generated by sequential dilution of liquors with further surfactant solution to obtain a series of endpoints.

In each case, binary mixtures were assessed in the weight to weight ratio phenol to terpene alcohol of 1:2.5. In some selected cases, the combinations were also tested at the weight ratio 1:1.

TABLE 29

Antibacterial activities of phenols and terpene alcohols alone and in combination in model surfactant solution, against *E. Coli*

| Phenolic compound concentration (% w/v) | Concentration of terpine alcohol $C_{ALC}$ (% w/v) | $\Delta$ OD 450 nm = $OD_{450}$ (time = 16 hours) – $OD_{450}$ (time zero) | | $\Delta$ OD 590 nm = $OD_{590}$ (time = 16 hours) – $OD_{590}$ (time zero) | | No. of replicates showing growth (out of 4) |
|---|---|---|---|---|---|---|
| | | Mean | Standard deviation | Mean | Standard deviation | |
| 0 | 0.5% (S)-(–) perillyl alcohol | −0.04 | 0.01 | 0.07 | 0.02 | 0 |
| 0 | 0.35% (S)-(–) perillyl alcohol | −0.18 | 0.26 | 0.19 | 0.20 | 1 |
| 0 | 0.25% (S)-(–) perillyl alcohol | −1.31 | 0.03 | 0.45 | 0.02 | 4 |
| 0 | 0.15% (S)-(–) perillyl alcohol | −1.45 | 0.04 | 0.34 | 0.02 | 4 |
| 0 | 0.2% (S)-(–) perillyl alcohol | −1.49 | 0.03 | 0.29 | 0.02 | 4 |
| 0 | 0.4% Isocyclo-Geraniol | −0.06 | 0.01 | 0.09 | 0.01 | 0 |
| 0 | 0.35% Isocyclo-Geraniol | −0.86 | 0.11 | 0.62 | 0.06 | 4 |
| 0 | 0.25% Isocyclo-Geraniol | −1.45 | 0.05 | 0.34 | 0.04 | 4 |
| 0 | 0.2% Isocyclo-Geraniol | −1.50 | 0.01 | 0.29 | 0.02 | 4 |
| 0 | 0.5% Floralol | −0.06 | 0.01 | 0.09 | 0.00 | 0 |
| 0 | 0.35% Floralol | −0.29 | 0.46 | 0.23 | 0.24 | 1 |
| 0 | 0.3% Floralol | −1.20 | 0.05 | 0.55 | 0.03 | 4 |
| 0 | 0.2% Floralol | −1.43 | 0.02 | 0.35 | 0.01 | 4 |
| 0 | 0.5% Dihydrofloralol | −0.06 | 0.01 | 0.10 | 0.01 | 0 |
| 0 | 0.35% Dihydrofloralol | −0.28 | 0.40 | 0.28 | 0.29 | 1 |
| 0 | 0.3% Dihydrofloralol | −1.15 | 0.04 | 0.60 | 0.04 | 4 |
| 0 | 0.2% Dihydrofloralol | −1.39 | 0.01 | 0.41 | 0.02 | 4 |
| 0.2% 4-chloro-3,5-dimethylphenol | 0 | −0.50 | 0.02 | 0.62 | 0.01 | 4 |
| 0.15% 4-chloro-3,5-dimethylphenol | 0 | −0.47 | 0.02 | 0.63 | 0.02 | 4 |
| 0.1% 4-chloro-3,5-dimethylphenol | 0 | −0.49 | 0.04 | 0.63 | 0.05 | 4 |
| 0.2% 4-chloro-3,5-dimethylphenol | 0.5% (S)-(–) perillyl alcohol | 0.25 | 0.02 | 0.26 | 0.01 | 0 |
| 0.175% 4-chloro-3,5-dimethylphenol | 0.4375% (S)-(–) perillyl alcohol | 0.24 | 0.04 | 0.20 | 0.03 | 0 |
| 0.15% 4-chloro-3,5-dimethylphenol | 0.375% (S)-(–) perillyl alcohol | 0.08 | 0.27 | 0.33 | 0.23 | 1 |
| 0.2% 4-chloro-3,5-dimethylphenol | 0.5% Isocyclo-Geraniol | 0.28 | 0.00 | 0.26 | 0.02 | 0 |

TABLE 29-continued

Antibacterial activities of phenols and terpene alcohols alone and in combination in model surfactant solution, against *E. Coli*

| Phenolic compound concentration (% w/v) | Concentration of terpine alcohol $C_{ALC}$ (% w/v) | Δ OD 450 nm = $OD_{450}$ (time = 16 hours) − $OD_{450}$ (time zero) Mean | Standard deviation | Δ OD 590 nm $OD_{590}$ (time = 16 hours) − $OD_{590}$ (time zero) Mean | Standard deviation | No. of replicates showing growth (out of 4) |
|---|---|---|---|---|---|---|
| 0.175% 4-chloro-3,5-dimethylphenol | 0.4375% Isocyclo-Geraniol | 0.12 | 0.27 | 0.37 | 0.21 | 1 |
| 0.15% 4-chloro-3,5-dimethylphenol | 0.375% Isocyclo-Geraniol | 0.08 | 0.29 | 0.34 | 0.22 | 1 |
| 0.2% 2-hydroxydiphenyl-methane | 0 | −0.51 | 0.02 | 0.63 | 0.02 | 4 |
| 0.15% 2-hydroxydiphenyl-methane | 0 | −0.49 | 0.02 | 0.64 | 0.01 | 4 |
| 0.1% 2-hydroxydiphenyl-methane | 0 | −0.51 | 0.02 | 0.62 | 0.02 | 4 |
| 0.2% 2-hydroxydiphenyl-methane | 0.5% Isocyclo-Geraniol | 0.25 | 0.01 | 0.26 | 0.03 | 0 |
| 0.157% 2-hydroxydiphenyl-methane | 0.4375% Isocyclo-Geraniol | 0.14 | 0.14 | 0.24 | 0.05 | 0 |
| 0.15% 2-hydroxydiphenyl-methane | 0.375% Isocyclo-Geraniol | −0.10 | 0.36 | 0.41 | 0.21 0.02 | 2 |
| 0.2% 4-hydroxydiphenyl-methane | 0 | −0.52 | 0.02 | 0.61 | 0.01 | 4 |
| 0.15% 4-hydroxydiphenyl-methane | 0 | −0.55 | 0.02 | 0.54 | 0.03 | 4 |
| 0.1% 4-hydroxydiphenyl-methane | 0 | −0.58 | 0.02 | 0.52 | 0.03 | 4 |
| 0.2% 4-hydroxydiphenyl-methane | 0.5% (S)-(−) perillyl alcohol | 0.25 | 0.02 | 0.27 | 0.05 | 0 |
| 0.175% 4-hydroxydiphenyl-methane | 0.4375% (S)-(−) perillyl alcohol | 0.19 | 0.04 | 0.30 | 0.09 | 0 |
| 0.15% 4-hydroxydiphenyl-methane | 0.375% (S)-(−) perillyl alcohol | 0.20 | 0.03 | 0.24 | 0.04 | 0 |
| 0.125% 4-hydroxydiphenyl-methane | 0.3125% (S)-(−) perillyl alcohol | −0.23 | 0.37 | 0.52 | 0.17 | 2 |
| 0.2% 4-hydroxydiphenyl-methane | 0.5% Isocyclo-Geraniol | 0.23 | 0.04 | 0.26 | 0.04 | 0 |
| 0.175% 4-hydroxydiphenyl-methane | 0.4375% Isocyclo-Geraniol | 0.17 | 0.04 | 0.22 | 0.03 | 0 |
| 0.15% 4-hydroxydiphenyl-methane | 0.375% Isocyclo-Geraniol | 0.17 | 0.03 | 0.22 | 0.04 | 0 |
| 0.125% 4-hydroxydiphenyl-methane | 0.3125% Isocyclo-Geraniol | −0.23 | 0.34 | 0.45 | 0.21 | 2 |
| 0.2% 4-hydroxydiphenyl-methane | 0.5% Floralol | 0.28 | 0.27 | 0.27 | 0.03 | 0 |
| 0.175% 4-hydroxydiphenyl-methane | 0.4375% Floralol | 0.25 | 0.23 | 0.25 | 0.03 | 0 |
| 0.15% 4-hydroxydiphenyl-methane | 0.375% Floralol | 0.22 | 0.20 | 0.23 | 0.04 | 0 |
| 0.125% 4-hydroxydiphenyl-methane | 0.3125% Floralol | 0.21 | 0.18 | 0.20 | 0.08 | 0 |

TABLE 29-continued

Antibacterial activities of phenols and terpene alcohols alone and in combination in model surfactant solution, against *E. Coli*

| Phenolic compound concentration (% w/v) | Concentration of terpine alcohol $C_{ALC}$ (% w/v) | $\Delta$ OD 450 nm = OD$_{450}$ (time = 16 hours) − OD$_{450}$ (time zero) Mean | Standard deviation | $\Delta$ OD 590 nm = OD$_{590}$ (time = 16 hours) − OD$_{590}$ (time zero) Mean | Standard deviation | No. of replicates showing growth (out of 4) |
|---|---|---|---|---|---|---|
| 0.1% 4-hydroxydiphenyl-methane | 0.25% Floralol | 0.18 | −0.24 | 0.47 | 0.21 | 2 |
| 0.2% 4-hydroxydiphenyl-methane | 0.5% Dihydrofloralol | 0.25 | 0.01 | 0.26 | 0.01 | 0 |
| 0.15% 4-hydroxydiphenyl-methane | 0.375% Dihydrofloralol | 0.18 | 0.02 | 0.22 | 0.05 | 0 |
| 0.125% 4-hydroxydiphenyl-methane | 0.3125% Dihydrofloralol | 0.16 | 0.03 | 0.21 | 0.03 | 0 |
| 0.1% 4-hydroxydiphenyl-methane | 0.25% Dihydrofloralol | −0.27 | 0.34 | 0.46 | 0.25 | 3 |
| 0.2% 5,6,7,8-tetrahydro-naphthalen-1-ol | 0 | −0.47 | 0.04 | 0.65 | 0.04 | 4 |
| 0.15% 5,6,7,8-tetrahydro-naphthalen-1-ol | 0 | −0.52 | 0.02 | 0.58 | 0.03 | 4 |
| 0.1% 5,6,7,8-tetrahydro-naphthalen-1-ol | 0 | −0.57 | 0.00 | 0.56 | 0.01 | 4 |
| 0.2% 5,6,7,8-tetrahydro-naphthalen-1-ol | 0.5% (S)-(−) perillyl alcohol | 0.25 | 0.02 | 0.27 | 0.03 | 0 |
| 0.15% 5,6,7,8-tetrahydro-naphthalen-1-ol | 0.375% (S)-(−) perillyl alcohol | 0.17 | 0.02 | 0.18 | 0.01 | 0 |
| 0.125% 5,6,7,8-tetrahydro-naphthalen-1-ol | 0.3125% (S)-(−) perillyl alcohol | 0.16 | 0.02 | 0.17 | 0.01 | 0 |
| 0.1% 5,6,7,8-tetrahydro-naphthalen-1-ol | 0.25% (S)-(−) perillyl alcohol | −0.24 | 0.36 | 0.50 | 0.19 | 2 |
| 0.2% 5,6,7,8-tetrahydro-naphthalen-1-ol | 0.5% Isocyclo-Geraniol | 0.29 | 0.03 | 0.28 | 0.01 | 0 |
| 0.15% 5,6,7,8-tetrahydro-naphthalen-1-ol | 0.375% Isocyclo-Geraniol | 0.20 | 0.02 | 0.23 | 0.04 | 0 |
| 0.125% 5,6,7,8-tetrahydro-naphthalen-1-ol | 0.3125% Isocyclo-Geraniol | 0.18 | 0.03 | 0.21 | 0.02 | 0 |
| 0.1% 5,6,7,8-tetrahydro-naphthalen-1-ol | 0.25% Isocyclo-Geraniol | −0.42 | 0.05 | 0.61 | 0.03 | 3 |
| 0.2% 5,6,7,8-tetrahydro-naphthalen-2-ol | 0 | −1.55 | 0.02 | 0.36 | 0.05 | 4 |
| 0.15% 5,6,7,8-tetrahydro-naphthalen-2-ol | 0 | −1.60 | 0.02 | 0.31 | 0.03 | 4 |
| 0.1% 5,6,7,8-tetrahydro-naphthalen-2-ol | 0 | −1.56 | 0.04 | 0.32 | 0.01 | 4 |
| 0.2% 5,6,7,8-tetrahydro-naphthalen-2-ol | 0.5% (S)-(−) perillyl alcohol | −0.06 | 0.03 | 0.07 | 0.03 | 0 |
| 0.15% 5,6,7,8-tetrahydro-naphthalen-2-ol | 0.375% (S)-(−) perillyl alcohol | −0.07 | 0.03 | 0.09 | 0.04 | 0 |
| 0.125% 5,6,7,8-tetrahydro-naphthalen-2-ol | 0.3125% (S)-(−) perillyl alcohol | −0.05 | 0.05 | 0.13 | 0.06 | 0 |
| 0.2% 5,6,7,8-tetrahydro-naphthalen-2-ol | 0.5% Isocyclo-Geraniol | −0.08 | 0.02 | 0.07 | 0.01 | 0 |

TABLE 29-continued

Antibacterial activities of phenols and terpene alcohols alone and in combination in model surfactant solution, against *E. Coli*

| Phenolic compound concentration (% w/v) | Concentration of terpine alcohol $C_{ALC}$ (% w/v) | $\Delta$ OD 450 nm = $OD_{450}$ (time = 16 hours) – $OD_{450}$ (time zero) | | $\Delta$ OD 590 nm $OD_{590}$ (time = 16 hours) – $OD_{590}$ (time zero) | | No. of replicates showing growth (out of 4) |
|---|---|---|---|---|---|---|
| | | Mean | Standard deviation | Mean | Standard deviation | |
| 0.175% 5,6,7,8-tetrahydro-naphthalen-2-ol | 0.4375% Isocyclo-Geraniol | −0.07 | 0.02 | 0.09 | 0.03 | 0 |
| 0.125% 5,6,7,8-tetrahydro-naphthalen-2-ol | 0.3125% Isocyclo-Geraniol | −0.07 | 0.05 | 0.12 | 0.06 | 0 |
| 0.2% 2-cyclopentyl-phenol | 0 | −0.52 | 0.01 | 0.61 | 0.01 | 4 |
| 0.15% 2-cyclopentyl-phenol | 0 | −0.56 | 0.01 | 0.54 | 0.02 | 4 |
| 0.1% 2-cyclopentyl-phenol | 0 | −0.57 | 0.01 | 0.56 | 0.01 | 4 |
| 0.2% 2-cyclopentyl-phenol | 0.5% (S)-(−) perillyl alcohol | 0.23 | 0.02 | 0.27 | 0.03 | 0 |
| 0.15% 2-cyclopentyl-phenol | 0.375% (S)-(−) perillyl alcohol | 0.17 | 0.24 | 0.24 | 0.05 | 0 |
| 0.125% 2-cyclopentyl-phenol | 0.3125% (S)-(−) perillyl alcohol | 0.13 | 0.21 | 0.21 | 0.04 | 0 |
| 0.1% 2-cyclopentyl-phenol | 0.25% (S)-(−) perillyl alcohol | −0.02 | 0.29 | 0.29 | 0.19 | 1 |
| 0.2% 2-cyclopentyl-phenol | 0.5% Isocyclo-Geraniol | 0.24 | 0.03 | 0.28 | 0.03 | 0 |
| 0.15% 2-cyclopentyl-phenol | 0.375% Isocyclo-Geraniol | 0.18 | 0.04 | 0.21 | 0.04 | 0 |
| 0.125% 2-cyclopentyl-phenol | 0.3125% Isocyclo-Geraniol | 0.12 | 0.02 | 0.18 | 0.02 | 0 |
| 0.1% 2-cyclopentyl-phenol | 0.25% Isocyclo-Geraniol | −0.14 | 0.32 | 0.40 | 0.25 | 2 |
| 0.2% 4-cyclopentyl-phenol | 0 | −0.40 | 0.01 | 0.70 | 0.02 | 4 |
| 0.15% 4-cyclopentyl-phenol | 0 | −0.45 | 0.01 | 0.65 | 0.01 | 4 |
| 0.125% 4-cyclopentyl-phenol | 0 | −0.49 | 0.02 | 0.62 | 0.02 | 4 |
| 0.2% 4-cyclopentyl-phenol | 0.5% (S)-(−) perillyl alcohol | 0.25 | 0.02 | 0.27 | 0.01 | 0 |
| 0.175% 4-cyclopentyl-phenol | 0.4375% (S)-(−) perillyl alcohol | 0.22 | 0.03 | 0.25 | 0.02 | 0 |
| 0.15% 4-cyclopentyl-phenol | 0.375% (S)-(−) perillyl alcohol | 0.20 | 0.04 | 0.21 | 0.01 | 0 |
| 0.125% 4-cyclopentyl-phenol | 0.3125% (S)-(−) perillyl alcohol | 0.00 | 0.40 | 0.40 | 0.22 | 1 |
| 0.2% 4-cyclopentyl-phenol | 0.5% Isocyclo-Geraniol | 0.20 | 0.01 | 0.26 | 0.02 | 0 |
| 0.175% 4-cyclopentyl-phenol | 0.4375% Isocyclo-Geraniol | 0.20 | 0.02 | 0.24 | 0.02 | 0 |
| 0.15% 4-cyclopentyl-phenol | 0.375% Isocyclo-Geraniol | 0.04 | 0.28 | 0.35 | 0.23 | 1 |

TABLE 29-continued

Antibacterial activities of phenols and terpene alcohols alone and in combination in model surfactant solution, against E. Coli

| Phenolic compound concentration (% w/v) | Concentration of terpine alcohol $C_{ALC}$ (% w/v) | $\Delta$ OD 450 nm = $OD_{450}$ (time = 16 hours) − $OD_{450}$ (time zero) Mean | Standard deviation | $\Delta$ OD 590 nm $OD_{590}$ (time = 16 hours) − $OD_{590}$ (time zero) Mean | Standard deviation | No. of replicates showing growth (out of 4) |
|---|---|---|---|---|---|---|
| 0.125% 4-cyclopentyl-phenol | 0.3125% Isocyclo-Geraniol | −0.25 | 0.31 | 0.60 | 0.22 | 3 |
| 0.2% 3-isopropyl-6-methylbenzene-1,2-diol | 0 | −0.53 | 0.01 | 0.53 | 0.01 | 4 |
| 0.175% 3-isopropyl-6-methylbenzene-1,2-diol | 0 | −0.51 | 0.01 | 0.53 | 0.01 | 4 |
| 0.15% 3-isopropyl-6-methylbenzene-1,2-diol | 0 | −0.50 | 0.02 | 0.56 | 0.03 | 4 |
| 0.2% 3-isopropyl-6-methylbenzene-1,2-diol | 0.5% (S)-(−) perillyl alcohol | −0.10 | 0.02 | 0.06 | 0.01 | 0 |
| 0.15% 3-isopropyl-6-methylbenzene-1,2-diol | 0.375% (S)-(−) perillyl alcohol | −0.09 | 0.01 | 0.06 | 0.02 | 0 |
| 0.125% 3-isopropyl-6-methylbenzene-1,2-diol | 0.3125% (S)-(−) perillyl alcohol | −0.11 | 0.05 | 0.11 | 0.06 | 0 |
| 0.2% 4-tert-butylbenzene-1,2-diol | 0 | −1.66 | 0.03 | 0.17 | 0.01 | 4 |
| 0.15% 4-tert-butylbenzene-1,2-diol | 0 | −1.63 | 0.05 | 0.20 | 0.02 | 4 |
| 0.125% 4-tert-butylbenzene-1,2-diol | 0 | −1.63 | 0.03 | 0.22 | 0.02 | 4 |
| 0.2% 4-tert-butylbenzene-1,2-diol | 0.5% (S)-(−) perillyl alcohol | −0.10 | 0.03 | 0.06 | 0.02 | 0 |
| 0.175% 4-tert-butylbenzene-1,2-diol | 0.4375% (S)-(−) perillyl alcohol | −0.10 | 0.04 | 0.09 | 0.04 | 0 |
| 0.15% 4-tert-butylbenzene-1,2-diol | 0.375% (S)-(−) perillyl alcohol | −0.79 | 0.37 | 0.47 | 0.15 | 2 |

TABLE 30

Minimum biocidal concentrations of antimicrobial components in 2.85% sodium cocoyl glycinate + 1.85% sodium lauroamphoacetate solution at pH 10

| Component | MBC (% w/v) |
|---|---|
| (S)-perillyl alcohol | 0.4 |
| Isocyclogeraniol | 0.4 |
| Floralol | 0.4 |
| Dihydrofloralol | 0.4 |
| 4-chloro-3,5-dimethylphenol | >0.2 |
| 4-chloro-2-isopropyl-5-methylphenol | >0.2 |
| 2-hydroxydiphenylmethane | >0.2 |
| 4-hydroxydiphenylmethane | >0.2 |
| 5,6,7,8-tetrahydronaphthalen-1-ol | >0.2 |
| 2-cyclopentylphenol | >0.2 |
| 4-cyclopentylphenol | >0.2 |
| 3-isopropyl-6-methylbenzene-1,2-diol | >0.2 |
| 4-tert-butylbenzene-1,2-diol | >0.2 |

Antimicrobial Efficacy of Actives Against *S. Aureus* in Water

*S. aureus* Bacterial stock was prepared as shown below and the antibacterial efficacy of the active was carried out as explained earlier for *E. Coli*. An overnight culture of *Staphy-* lococcus aureus (10788 strain) was inoculated onto a Tripticase Soy Agar (TSA) plate and grown for ca. 18 hrs at 37° C. The culture of S. aureus was washed from the plate using sterile saline (0.85% NaCl) solution and a sterile spreader and suspended in 50 ml saline. This suspension was separated into equal volumes and centrifuged at 4000 rpm for 15 minutes. Following centrifugation the pellet was re-suspended in saline to give a final concentration of 0.35 $OD_{620}$ equivalent to about $10^8$ cells per milliliter for this particular organism. Here, $OD_{620}$ indicates the absorbance of a sample in a cuvette of 1.0 cm path length at a wavelength, of 620 nm. This bacterial stock was used for assaying against antimicrobial actives (in triplicate).

Antibacterial activities of certain combinations as per the invention against S. aureus is summarised below:

TABLE 31

| Composition | S. aureus 6538 Log Reduction |
|---|---|
| 0.1% 3 isopropyl 6 methyl catechol (IPMC) | −0.07 |
| 0.1% IPMC +).2% perillyl alcohol | 6.8 |
| 0.2% perillyl alcohol | 0.22 |
| 0.05% cyclopentyl phenol + 0.25 Perillyl alcohol | 3.78 |
| 0.25 Perillyl alcohol | 0.5 |

The invention claimed is:

1. A synergistic microbicidal composition comprising 4-chloro-3,5-dimethylphenol and 2-(4-methylcyclohex-3-enyl)propan-1-ol in a weight ratio from 1/0.05 to 1/2.5.

2. A synergistic microbicidal composition comprising 4-chloro-3,5-dimethylphenol and (4S)-(4-(prop-1-en-2-yl)cyclohex-1-enyl)methanol in a weight ratio from 1/0.03 to 1/0.08 or 1/0.13 to 1/50.

3. A synergistic microbicidal composition comprising 4-chloro-3,5-dimethylphenol and 2,4,6-trimethyl-3-cyclohexene-1-methanol in a weight ratio from 1/0.13 to 1/0.17 or 1/0.33 to 1/6.

4. A synergistic microbicidal composition comprising: (a) at least one microbicide selected from the group consisting of 2-hydroxydiphenylmethane and 4-hydroxydiphenylmethane, and (b) at least one microbicide selected from the group consisting of 2-(4-methylcyclohex-3-enyl)propan-1-ol, (4S)-(4-(prop-1-en-2-yl)cyclohex-1-enyl)methanol and 2,4,6-trimethyl-3-cyclohexene-1-methanol; excluding a combination of 4-hydroxydiphenylmethane and (4S)-(4-(prop-1-en-2-yl)cyclohex-1-enyl)methanol; wherein a weight ratio of 2-hydroxydiphenylmethane to 2-(4-methylcyclohex-3-enyl)propan-1-ol is 1/0.04 to 1/0.08, a weight ratio of 2-hydroxydiphenylmethane to (4S)-(4-(prop-1-en-2-yl)cyclohex-1-enyl)methanol is from 1/0.25 to 1/0.5, a weight ratio of 2-hydroxydiphenylmethane to 2,4,6-trimethyl-3-cyclohexene-1-methanol is from 1/1 to 1/1.5, a weight ratio of 4-hydroxydiphenylmethane to 2-(4-methylcyclohex-3-enyl)propan-1-ol is 1/0.08 to 1/0.5 and a weight ratio of 4-hydroxydiphenylmethane to 2,4,6-trimethyl-3-cyclohexene-1-methanol is from 1/1 to 1/10.

5. A synergistic microbicidal composition comprising: (a) at least one microbicide selected from the group consisting of 5,6,7,8-tetrahydronaphthalen-1-ol and 5,6,7,8-tetrahydronaphthalen-2-ol; and (b) at least one microbicide selected from the group consisting of 2-(4-methylcyclohex-3-enyl)propan-1-ol, (4S)-(4-(prop-1-en-2-yl)cyclohex-1-enyl)methanol and 2,4,6-trimethyl-3-cyclohexene-1-methanol; wherein a weight ratio of 5,6,7,8-tetrahydronaphthalen-1-ol to 2-(4-methylcyclohex-3-enyl)propan-1-ol is from 1/0.25 to 1/0.5, a weight ratio of 5,6,7,8-tetrahydronaphthalen-1-ol to (4S)-(4-(prop-1-en-2-yl)cyclohex-1-enyl)methanol is from 1/0.19 to 1/10, a weight ratio of 5,6,7,8-tetrahydronaphthalen-1-ol to 2,4,6-trimethyl-3-cyclohexene-1-methanol is from 1/0.25 to 1/5, a weight ratio of 5,6,7,8-tetrahydronaphthalen-2-ol to 2-(4-methylcyclohex-3-enyl)propan-1-ol is from 1/0.04 to 1/0.33, a weight ratio of 5,6,7,8-tetrahydronaphthalen-2-ol to (4S)-(4-(prop-1-en-2-yl)cyclohex-1-enyl)methanol is from 1/0.19 to 1/5, a weight ratio of 5,6,7,8-tetrahydronaphthalen-2-ol to 2,4,6-trimethyl-3-cyclohexene-1-methanol is from 1/0.04 to 1/10.

6. A synergistic microbicidal composition comprising: (a) at least one microbicide selected from the group consisting of 2-cyclopentylphenol and 4-cyclopentylphenol; and (b) at least one microbicide selected from the group consisting of 2-(4-methylcyclohex-3-enyl)propan-1-ol, (4S)-(4-(prop-1-en-2-yl)cyclohex-1-enyl)methanol and 2,4,6-trimethyl-3-cyclohexene-1-methanol; wherein a weight ratio of 2-cyclopentylphenol to 2-(4-methylcyclohex-3-enyl)propan-1-ol is 1/0.25, a weight ratio of 2-cyclopentylphenol to (4S)-(4-(prop-1-en-2-yl)cyclohex-1-enyl)methanol is from 1/0.38 to 1/50, a weight ratio of 2-cyclopentylphenol to 2,4,6-trimethyl-3-cyclohexene-1-methanol is from 1/0.06 to 1/0.17 or 1/0.33 to 1/3, wherein a weight ratio of 4-cyclopentylphenol to 2-(4-methylcyclohex-3-enyl)propan-1-ol is from 1/0.13 to 1/3.33, a weight ratio of 4-cyclopentylphenol to (4S)-(4-(prop-1-en-2-yl)cyclohex-1-enyl)methanol is from 1/0.06 to 1/2.5, a weight ratio of 4-cyclopentylphenol to 2,4,6-trimethyl-3-cyclohexene-1-methanol is from 1/0.5 to 1/1.25.

7. A synergistic microbicidal composition comprising, (a) at least one microbicide selected from the group consisting of 3-isopropyl-6-methylbenzene-1,2-diol and 4-tert-butylbenzene-1,2-diol; and (b) at least one microbicide selected from the group consisting of 2-(4-methylcyclohex-3-enyl)propan-1-ol, (4S)-(4-(prop-1-en-2-yl)cyclohex-1-enyl)methanol, 2,4,6-trimethyl-3-cyclohexene-1-methanol; wherein a weight ratio of 3-isopropyl-6-methylbenzene-1,2-diol to 2-(4-methylcyclohex-3-enyl)propan-1-ol is 1/0.03 or 1/0.13, a weight ratio of 3-isopropyl-6-methylbenzene-1,2-diol to (4S)-(4-(prop-1-en-2-yl)cyclohex-1-enyl)methanol is from 1/0.13 to 1/150, a weight ratio of 3-isopropyl-6-methylbenzene-1,2-diol to 2,4,6-trimethyl-3-cyclohexene-1-methanol is from 1/0.08 to 1/75, a weight ratio of 4-tert-butylbenzene-1,2-diol to 2-(4-methylcyclohex-3-enyl)propan-1-ol is 1/0.13, a weight ratio of 4-tert-butylbenzene-1,2-diol to (4S)-(4-(prop-1-en-2-yl)cyclohex-1-enyl)methanol is 1/0.03 or 1/0.13, and a weight ratio of 4-tert-butylbenzene-1,2-diol to 2,4,6-trimethyl-3-cyclohexene-1-methanol is from 1/0.04 to 1/0.06 or 1/0.75 to 1/3.75.

8. The synergistic microbicidal composition according to any one of the preceding claims comprising from 1 to 80% by weight of one or more surfactants.

9. The synergistic microbicidal according to claim 8 wherein the one or more surfactants are selected from the group consisting of soaps, alkyl sulphates and linear alkyl benzene sulphonates.

* * * * *